(12) United States Patent
Li et al.

(10) Patent No.: US 7,663,757 B2
(45) Date of Patent: Feb. 16, 2010

(54) APPARATUS AND METHOD FOR OBTAINING A REFLECTANCE PROPERTY INDICATION OF A SAMPLE

(75) Inventors: Wei Li, Edmonton (CA); Ross Chow, Sherwood Park (CA); Jim Boyd Curtis, Edmonton (CA); Xiaocai Joyce Chen, Edmonton (CA)

(73) Assignee: Alberta Research Council Inc., Edmonton (CA)

( * ) Notice: Subject to any disclaimer, the term of this patent is extended or adjusted under 35 U.S.C. 154(b) by 279 days.

(21) Appl. No.: 11/527,993

(22) Filed: Sep. 27, 2006

(65) Prior Publication Data

US 2008/0079943 A1 Apr. 3, 2008

(51) Int. Cl.
*G01N 21/55* (2006.01)
(52) U.S. Cl. .................................. 356/445
(58) Field of Classification Search ........... 356/445, 356/446, 237.1–237.5; 250/227.29, 214 R, 250/224
See application file for complete search history.

(56) References Cited

U.S. PATENT DOCUMENTS

| | | | |
|---|---|---|---|
| 3,020,196 A * | 2/1962 | Schuber | 162/78 |
| 4,019,819 A * | 4/1977 | Lodzinski | 356/73 |
| 4,040,743 A | 8/1977 | Villaume et al. | |
| 4,344,709 A * | 8/1982 | Provder et al. | 356/445 |
| 4,729,657 A | 3/1988 | Cooper et al. | |
| 5,792,942 A | 8/1998 | Hosokawa | |
| 5,842,150 A | 11/1998 | Renberg et al. | |
| 5,926,262 A * | 7/1999 | Jung et al. | 356/73 |
| 6,594,013 B2 | 7/2003 | Thakur et al. | |
| 2003/0155092 A1 | 8/2003 | Badenlid et al. | |
| 2003/0214655 A1 * | 11/2003 | Weiss et al. | 356/402 |
| 2004/0252883 A1 * | 12/2004 | Johansson et al. | 382/162 |

FOREIGN PATENT DOCUMENTS

CA 1048293 2/1979

(Continued)

OTHER PUBLICATIONS

Trotter, A.B. et. al., "An On-Line Pulp Bale Brightness Meter for Pulp Bale Information Systems," Proceedings of the 47th Appita Annual General Conference, Rotorua, New Zealand, 1993, vol. 2, pp. 651-655.

(Continued)

*Primary Examiner*—Tarifur R. Chowdhury
*Assistant Examiner*—Isiaka O Akanbi
(74) *Attorney, Agent, or Firm*—Rodman & Rodman; Terrence N. Kuharchuk

(57) ABSTRACT

A method for obtaining a reflectance property indication of a sample which includes making a reflectance measurement of the sample and correcting the reflectance measurement in order to obtain the reflectance property indication. The reflectance measurement represents an observed reflectance of the sample, the reflectance property indication represents a standardized reflectance of the sample, and correcting the reflectance measurement accounts for a difference between the standardized reflectance and the observed reflectance. An apparatus for making a reflectance measurement of a sample which includes a housing defining a viewing port, a temperature control mechanism for controlling the temperature within the interior of the housing, and an optical reflectometer contained within the interior of the housing. The reflectometer has a measurement direction and is movable within the housing so that the measurement direction can be selectively aligned with the viewing port.

26 Claims, 9 Drawing Sheets

FOREIGN PATENT DOCUMENTS

| | | |
|---|---|---|
| CA | 1299386 | 4/1992 |
| CA | 2423756 | 9/2004 |
| GB | 2054845 | 2/1981 |

OTHER PUBLICATIONS

Morgan, Stephen et. al., "The Development and Mill Application of a Real Time, On-Line Pulp Dirt Sensor," Proceedings of the Wastepaper VII Conference, Chicago, Illinois, USA, 1996.

Nilsson, C.M. et. al., "Application of Optical Spectroscopy to Paper Production," SPIE vol. 3824, pp. 318-325.

Malmstrom, E., "Quality Measurement in Real Time has Become a Reality," Svensk papperstidn, vol. 102, No. 9, 1999, pp. 38-39.

Lobosco, Vinicius et. al., "An elastic/viscoplastic model of the fibre network stress in wet pressing: Part 2 accounting for pulp properties and web temerature," Nordic Pulp and Paper Research Journal, V. 16, No. 4, 2001, pp. 313-318.

Komarov, V.I. et. al., "Usage of phenomenological model of a deforming for forecasting of deformation capability of unbleached kraft pulp," Tselliuloza, Bumaga, Karton/Pulp, Paper, Board, No. 9-10, 2000, pp. 38-41.

\* cited by examiner

APPARATUS AND METHOD FOR OBTAINING A REFLECTANCE PROPERTY INDICATION OF A SAMPLE

TECHNICAL FIELD

An apparatus and a method for obtaining a reflectance property indication of a sample.

BACKGROUND OF THE INVENTION

In their efforts to meet the demands of today's competitive and worldwide market structures, producers of paper pulp are confronted with stringent requirements for their pulp product to be of a high, consistent and well-documented quality. Pulp producers use a number of optical and physical properties to specify the grade of their product. Tests according to established industry standards are commonly used to determine various pulp properties, such as brightness, opacity, bulk, shive content, elasticity, tensile strength, moisture etc.

A pulp brightness test is a test which provides an indication of a reflectance property of a pulp sample. More particularly, a pulp brightness test is typically a test which provides an indication of the reflectance of blue light by the pulp. A pulp brightness test may be conducted using a number of different methods and according to a number of different standards.

For example, a pulp brightness test may be conducted as a directional brightness test in which a light source comprising a single light is directed at a pulp sample at a specific angle and the reflectance of the pulp is measured as the light is reflected from the pulp. A standard relating to a directional brightness test is the Technical Association for the Pulp, Paper and Converting Industry (TAPPI) standard T 452.

Alternatively, a pulp brightness test may be conducted as a diffuse brightness test in which a light source comprising one or more lights is directed within a diffusing device such as an integrating sphere and is caused to reflect within the diffusing device before reaching the pulp sample. Standards relating to diffuse brightness tests include TAPPI standard T 525, International Standards Organization (ISO) standard ISO 2469 and ISO standard ISO 2470.

Pulp brightness according to ISO standard ISO 2470 is characterized by a diffuse blue reflectance factor of the pulp, which is defined as the amount of diffuse blue light reflected by the pulp (i.e., reflectance of the pulp) in a given direction expressed as a percentage of the reflectance by a perfect reflecting diffuser under the same conditions. Pulp brightness according to ISO standard ISO 2470 is therefore often referred to as the "diffuse blue reflectance factor" or "ISO brightness".

Currently, pulp producers evaluate pulp brightness by manually sampling pulp bales on a pulp finishing line and conducting one or more of the standard tests. Drawbacks inherent to this approach include obvious sample limitations, as well as time delays. For example, it may be estimated that the quality of sixty bales of pulp could conceivably be assessed by using only six grams of a pulp sample. Furthermore, three to four hours are needed to obtain the results of the quality tests.

In view of the shortcomings associated with the traditional methods of assessing the properties of pulp samples, various methods have been proposed to circumvent the intrinsic problems associated with the standard tests. For example, the prior art teaches different approaches to on-line monitoring of the quality of pulp samples.

Trotter, A. B. et al "An On-Line Pulp Bale Brightness Meter for Pulp Bale Information Systems" (Proceedings of the 47$^{th}$ Appita Annual Conference; Rotorua, New Zealand; 1993, Vol. 2, p. 651-655) describes a brightness meter for measuring the brightness of pulp bales, and a method for on-line measurements of pulp brightness. Like the lab pulp brightness meter (based on ISO standard ISO 2469 and ISO 2470), a measuring head is built around an integrating sphere to provide diffuse light source for the measurement. For on-line operation the measuring head is mounted on a platform that is raised and lowered by two air pistons. The whole unit is housed in a rectangular box and constructed so that the box opens by rotating or pivoting a covering part of the box. A lid portion of the covering part carries a reflectance tile on its underside which, as well as covering the measuring port when the box is closed, allows the system to check its response against a tile of known reflectance.

Morgan, Stephen and Jeune, Max, "The Development and Mill Application of a Real Time, On-Line Pulp Dirt Sensor" (Proceedings of the Wastepaper VII Conference; Chicago, Ill., U.S.A., 1996) describes a system for detecting specks and dirt particles in a paper or pulp sheet.

Nilsson, C. M. et al, "Application of Optical Spectroscopy to Paper Production" (SPIE Vol. 3824, p. 318-325) describes the application of fluorescence monitoring to study the relative shrinking of paper during drying.

Malmström, E., "Quality Measurement in Real Time has Become a Reality" Svensk Papperstidn., Vol. 102, No. 9, p. 38-39 (1999) describes a system for measuring the properties of pulp in real time which combines NIR-spectroscopy with multivariate data examination, but does not appear to utilize reflectance measurements.

U.S. Patent Application Publication No. US 2003/0155092 A1 (Badenlid et al) describes a method for predicting properties of a product that consists of cellulose-fiber-based pulp, paper or paperboard by means of spectroscopic measurements in a selected spectrum in the wavelength range of 200-25000 nm. In the method, a sample quantity of fiber is extracted and diluted prior to analysis, following which one partial flow of the diluted sample quantity is dewatered, dried and used for spectroscopic measurements, while a second partial flow of the diluted sample quantity is used for analysis of physical fiber data by means of image analysis. The sample quantity may be extracted for analysis at-line or on-line in a process line.

U.S. Pat. No. 4,040,743 (Villaume et al) describes a method and an apparatus for measuring the brightness and/or consistency of a pulp slurry. The apparatus is comprised of an optical probe which introduces light energy into the pulp slurry. The light energy is transmitted, back-scattered and reflected orthogonally. Three signals are provided which correspond to the transmitted, back-scattered and reflected light energy. The signals are ratioed against a reference signal which corresponds to the intensity of the light energy introduced into the pulp slurry to provide three outputs proportional to the difference between the difference between the reference signal and the provided signals. The outputs are used to provide independent measurements of brightness of the pulp slurry and consistency of the pulp slurry.

U.S. Pat. No. 5,792,942 (Hosokawa) describes an apparatus for determining properties of a slurry material such as sludge and pulp slurry which is adapted to obtain samples for analysis directly out of a slurry transfer passage or a slurry storage tank.

There remains a need for an apparatus and a method for obtaining a reflectance property indication of a lignocellulosic material which provides an alternative to the apparatus and methods disclosed in the prior art.

SUMMARY OF THE INVENTION

The present invention relates to a method and an apparatus for obtaining a reflectance property indication of a sample. More particularly, the invention relates to a method and apparatus for making a reflectance measurement of a sample and obtaining a reflectance property indication from the reflectance measurement. The reflectance measurement represents an observed reflectance of the sample under actual conditions and the reflectance property indication represents a standardized reflectance of the sample under standard conditions. The method involves correcting the reflectance measurement to account for a difference between the standardized reflectance of the sample and the observed reflectance of the sample.

The sample may be comprised of any material for which a reflectance measurement may be made. Preferably the sample is comprised of a lignocellulosic material, such as paper, board or pulp. In a preferred embodiment, the sample is comprised of a lignocellulosic pulp.

In a particular method aspect, the invention is a method for obtaining a reflectance property indication of a sample, wherein the sample is comprised of a lignocellulosic material, the method comprising:

(a) providing an optical reflectometer;
 (b) relatively positioning the sample and the reflectometer;
 (c) making a reflectance measurement of the sample with the reflectometer, wherein the reflectance measurement represents an observed reflectance of the sample; and
 (d) correcting the reflectance measurement in order to obtain the reflectance property indication, wherein the reflectance property indication represents a standardized reflectance of the sample and wherein correcting the reflectance measurement accounts for a difference between the standardized reflectance of the sample and the observed reflectance of the sample.

In a particular apparatus aspect, the invention is an apparatus for making a reflectance measurement of a sample comprising a lignocellulosic material, the apparatus comprising:

(a) a housing, the housing defining an interior of the housing, an exterior of the housing and a viewing port for facilitating viewing of the sample from the interior of the housing when the sample is located at the exterior of the housing and adjacent to the viewing port;
 (b) a temperature control mechanism for controlling a temperature within the interior of the housing; and
 (c) an optical reflectometer contained within the interior of the housing for making a reflectance measurement of the sample, wherein the reflectometer has a measurement direction, and wherein the reflectometer is movable within the housing so that the measurement direction may be selectively aligned with the viewing port.

The reflectance measurement may be comprised of any type of measurement of reflectance, and may be performed using any method for obtaining a measurement of reflectance of a material. For example, the reflectance measurement may be a measurement of direct reflectance or may be a measurement of diffuse reflectance. The reflectance measurement may be a measurement of total reflectance or may be a measurement of reflectance relating to a particular range of wavelengths, such as for example blue reflectance. In the preferred embodiment the reflectance measurement is a measurement of diffuse reflectance and may be a measurement of either total diffuse reflectance or diffuse blue reflectance.

An optical reflectometer is defined as an instrument for measuring the reflectance of reflecting surfaces, and the reflectometer of the invention may therefore be comprised of any structure, device or apparatus which is capable of measuring the reflectance of reflecting surfaces.

The reflectance property indication may be comprised of any indication which represents a standardized reflectance of the sample. The standardized reflectance may relate to a known standard such as TAPPI standard T 452 or ISO standards ISO 2469 and ISO 2470, or the standardized reflectance may represent any other standard, such as for example an arbitrary standard, a local standard or an application specific standard. The reflectance property indication may represent an absolute standardized reflectance, or alternatively the reflectance property indication may represent a relative standardized reflectance such as a diffuse blue reflectance factor or ISO brightness.

Preferably the reflectance measurement is made using an apparatus and method which is compatible with the reflectance property indication which is sought to be obtained. For example, if the reflectance property indication is intended to be substantially equivalent to an indication provided by a known standard, the reflectance measurement is preferably made using a method and apparatus which closely approximates the method and apparatus prescribed by the known standard.

In a preferred embodiment, the reflectance measurement is a measurement of a diffuse reflectance and is made using a reflectometer which is similar or identical to the apparatus prescribed by ISO standard ISO 2469 and/or ISO standard ISO 2470. The reflectance measurement may be expressed as a diffuse reflectance (as in ISO standard ISO 2469) or as a diffuse blue reflectance (as in ISO standard ISO 2470).

Similarly, in the preferred embodiment, the goal of the reflectance property indication is to replicate a reflectance property indication obtained by using ISO standard ISO 2469 and ISO standard ISO 2470, and is therefore preferably substantially equivalent to a diffuse reflectance factor (as in ISO standard ISO 2469) or a diffuse blue reflectance factor (as in ISO standard ISO 2470), which is sometimes referred to as "ISO brightness".

As a result, in the preferred embodiment either the reflectance measurement directly provides a measurement of diffuse blue reflectance through the use of filters etc. or the reflectance measurement provides a measurement of total diffuse reflectance which may be processed as provided for in ISO standard ISO 2470 to provide a measurement of diffuse blue reflectance, thereby facilitating obtaining a diffuse blue reflectance factor as the reflectance property indication.

The invention may be used in any environment in which it is advantageous, convenient or desirable to obtain a reflectance measurement under actual conditions and to obtain a reflectance property indication by correcting the reflectance measurement to account for a difference between the standardized reflectance of the sample under standard conditions and the actual reflectance of the sample under the actual conditions.

In the preferred embodiment, the invention is used to obtain a reflectance property indication of a lignocellulosic pulp located on a pulp production finishing line. More particularly, in the preferred embodiment the pulp production finishing line is comprised of a forming press for producing a formed pulp product and a bale press for producing a pulp bale, and the lignocellulosic pulp is comprised of the formed pulp product.

In the preferred embodiment, the reflectance measurement is made of an underside of the formed pulp product as the formed pulp product moves along the pulp production finishing line.

Making the reflectance measurement may be comprised of making a single measurement of the observed reflectance of the sample. Preferably, however, the reflectance measurement is comprised of an average of a plurality of measurements of the observed reflectance of the sample.

In the preferred embodiment, the sample defines a measurement surface and making the reflectance measurement is comprised of making a plurality of measurements of the observed reflectance of the sample over the measurement surface and determining an average of the measurements of the observed reflectance as the reflectance measurement. In the preferred embodiment where the sample is comprised of a formed pulp product, the measurement surface of the sample is comprised of an underside of the formed pulp product.

Correcting the reflectance measurement may be comprised making any correction of the reflectance measurement which accounts for a difference between the standardized reflectance of the sample and the observed reflectance of the sample. The nature of the corrections which are made of the reflectance measurement may vary depending upon the nature of the reflectance measurement, the nature of the reflectance property indication, the nature of the standard conditions, and the nature and extent to which the standard conditions are different from the actual conditions.

In the preferred embodiment, correcting the reflectance measurement is comprised of one or more of making a geometry correction, making a texture correction, and making a drift correction of the reflectance measurement.

The geometry correction is made to correct for a difference between a standard geometry between the sample and the reflectometer and an actual geometry between the sample and the reflectometer. For example, if the reflectance measurement is a measurement of direct reflectance, the geometry correction may account for a difference between the standard angle of incidence of the light source and the actual angle of incidence of the light source, or may account for a difference between a standard orientation of the sample and an actual orientation of the sample.

In the preferred embodiment where the reflectance measurement is a measurement of diffuse reflectance, the geometry correction is comprised of a distance correction to account for a difference between a standard distance between the sample and the reflectometer and an actual distance between the sample and the reflectometer. In the preferred embodiment the actual distance between the sample and the reflectometer is defined as the difference between the measurement surface of the sample and the receptor of the reflectometer.

Making the distance correction of the reflectance measurement may be comprised of obtaining a distance measurement of the actual distance between the sample and the reflectometer. The distance measurement may be comprised of a single measurement of the actual distance between the sample and the reflectometer. Preferably, however, the distance measurement is comprised of an average of a plurality of measurements of the actual distance between the sample and the reflectometer.

In the preferred embodiment where the sample defines a measurement surface, making the distance measurement is comprised of making a plurality of measurements of the actual distance between the measurement surface and the reflectometer and determining an average actual distance between the measurement surface and the reflectometer as the reflectance measurement.

The observed reflectance of the sample is generally inversely proportional to the actual distance between the sample and the reflectometer. In other words, the observed reflectance of the sample will generally decrease as the actual distance between the sample and the reflectometer increases.

As a result, making the distance correction may be comprised of;
(a) obtaining a distance measurement of the actual distance between the sample and the reflectometer;
(b) establishing a distance data point consisting of the actual distance and the reflectance measurement;
(c) selecting a distance correction function which fits with the distance data point; and
(d) making the distance correction from the selected distance correction function.

The standard distance may be defined by the standard which governs the determination of the standard reflectance of the sample. For example, in the preferred embodiment the standard distance may be defined by ISO standard ISO 2469 and/or ISO standard ISO 2470.

In the preferred embodiment, a plurality of distance correction functions are developed by evaluating under substantially standard conditions the reflectance of a number of handsheet samples of different ISO brightness prepared in accordance with a standard such as TAPPI standard TAPPI 218, while varying the distance between the samples and the reflectometer.

The appropriate distance correction function can then be selected by seeking the best fit between the distance correction functions and the distance data point. The selected distance correction function may be a distance correction function developed from a particular handsheet, or may be an interpolated or extrapolated distance correction function.

Once the appropriate distance correction function is selected, the distance corrected reflectance can be identified from the selected distance correction function as the reflectance which corresponds to the standard distance between the sample and the reflectometer.

The texture correction is made to correct for a difference between a standard texture of the sample and an actual texture of the sample. The texture correction may not be required where the sample has been prepared in accordance with the procedures prescribed by the relevant standard. In the preferred embodiment, however, the formed pulp product is not prepared in accordance with the procedures prescribed by ISO standard ISO 2469 and/or ISO standard ISO 2470, with the result that the texture correction is typically required.

Generally, the measurement surface of the formed pulp product will be less smooth than the surface of a prepared standard sample which is used in ISO standard ISO 2470, with the result that the reflectance of the formed pulp product will generally be higher than the reflectance of a prepared standard sample of an equivalent type or grade of pulp.

In the preferred embodiment, the texture of the measurement surface is dependent upon the characteristics of the forming press and its operating parameters, as well as upon the characteristics of the pulp of which the formed pulp product is comprised.

The texture correction may be made using any method which provides a relationship between reflectance of the sample and texture of the sample. The texture correction may therefore be made using methods which quantify the texture of the sample.

As a result, making the texture correction may be comprised of:
(a) obtaining a measurement of the actual texture of the sample;
(b) establishing a texture data point: consisting of the actual texture and the reflectance measurement;

(c) selecting a texture correction function which fits with the texture data point; and (d) making the texture correction from the selected texture correction function.

The measurement of the actual texture of the sample may be obtained in any suitable manner. In the preferred embodiment, obtaining a measurement of the actual texture of the sample is comprised of obtaining a measurement of a distance standard deviation of the measurements of the actual distance between the measurement surface and the reflectometer.

In the preferred embodiment, a plurality of texture correction functions are developed by evaluating the reflectance of a plurality of sets of the formed pulp product, wherein the sets of formed pulp products exhibit a range of ISO brightness. The observed reflectance of a set of formed pulp products having an equivalent ISO brightness but exhibiting different values of the distance standard deviation is used to develop each texture correction function.

The appropriate texture correction function can then be selected by seeking the best fit between the texture correction functions and the texture data point. The selected texture correction function may be a texture correction function developed from a particular set of formed pulp products, or may be an interpolated or extrapolated texture correction function.

Once the appropriate texture correction function is selected, the texture corrected reflectance can be identified from the selected texture correction function as the reflectance which corresponds to a standard value of the distance standard deviation, wherein the standard value is the distance standard deviation of a prepared standard sample.

The drift correction is made to account for a drift in an intensity of the light source which is used to make the reflectance measurement. The drift correction may also account for a change or drift in a sensitivity of the reflectometer.

The drift correction may be made using any method which provides a relationship between reflectance of the sample and a drift in the intensity of the light source and/or the sensitivity of the reflectometer. For example, the drift correction may be comprised of referencing the reflectance measurement of the sample to a standard reflectance of one or more reference standards.

As a first example, the reflectance measurement may be made using a reflectance scale which is established with reference to a high reflectance reference standard and a low reflectance reference standard. The reference standards exhibit a known standard reflectance and can therefore be used to determine an upper limit and a lower limit of the reflectance scale. Over time in the practice of the invention the reflectance of the reference standards as measured by the reflectometer may deviate from the known standard reflectances, due to deterioration of the light source, the presence of contaminants, or problems with the reflectometer.

As a result, making the drift correction may be comprised of adjusting the reflectance scale so that the reflectance measurements made by the reflectometer of samples are representative of the true observed reflectance of the samples.

Adjusting the reflectance scale may be comprised of:

(a) obtaining a high reflectance standard measurement from a high reflectance reference standard;

(b) obtaining a low reflectance standard measurement from a low reflectance reference standard; and (c) adjusting the reflectance scale by comparing the high reflectance standard measurement and the low reflectance standard measurement with the reflectance scale.

As a second example, the drift correction may be made by referencing the reflectance measurement of the sample to a standard reflectance of one or more reference standards.

In the preferred embodiment, the drift correction is made by referencing the reflectance measurement of the sample to the high reflectance reference standard. In the preferred embodiment, the low reflectance reference standard may be used as a backup for making the drift correction or may be used to verify the observed reflectance of the high reflectance reference standard.

In the preferred embodiment, the method of the invention is performed within an operating range of light intensity so that the drift correction can be made to reflectance measurements which are within the operating range.

In the preferred embodiment the operating range is defined by an observed reflectance of the high reflectance reference standard. For example, the operating range of the method may be defined by a reflectance range as exhibited by the high reflectance reference standard under different levels of intensity of the light source. The high reflectance reference standard will exhibit a standard reference reflectance which will be within the operating range of the method.

As a result, in the preferred embodiment, making the drift correction may be comprised of:

(a) obtaining a reference reflectance measurement of a reference standard;

(b) establishing a drift data point consisting of the reference reflectance measurement and the reflectance measurement;

(c) selecting a drift correction function which fits with the drift data point; and (d) making the drift correction from the selected drift correction function.

In the preferred embodiment, a plurality of drift correction functions are developed by evaluating under substantially standard conditions the reflectance of a number of handsheet samples of different ISO brightness prepared in accordance with a standard such as TAPPI standard TAPPI 218, while varying the intensity of the light source. In the preferred embodiment, the intensity of the light source is varied within the operating range of the method.

The appropriate drift correction function can then be selected by seeking the best fit between the distance correction functions and the drift data point. The selected drift correction function may be a drift correction function developed from a particular handsheet or may be an interpolated or extrapolated drift correction function.

Once the appropriate drift correction function is selected, the drift corrected reflectance can be identified from the selected drift correction function as the reflectance which corresponds to the standard reference reflectance the high reflectance reference standard.

The corrections to the reflectance measurement may be expressed in any manner. For example, a correction may be expressed as a corrected reflectance measurement, as a percentage of the reflectance measurement being corrected, as a fraction of the reflectance measurement being corrected, or as an amount to be added to or subtracted from the reflectance measurement being corrected, etc.

The corrections to the reflectance measurement may be made in any order. The corrections to the reflectance measurement may be made separately, in which case each correction is expressed relative to the original reflectance measurement. Alternatively, the corrections to the reflectance measurement may be made sequentially, in which case the second and subsequent corrections are made to the reflectance measurement as corrected by a previous correction or corrections. As a result, correcting the reflectance measurement may involve correcting the reflectance measurement as made by the reflectometer, or correcting the reflectance measurement as corrected by a previous correction or corrections.

A different correction to be made to the reflectance measurement may be determined for each reflectance measurement, or a correction to be made to the reflectance measurement may be determined periodically and then applied to a plurality of reflectance measurements.

In the preferred embodiment, a different distance correction and texture correction are determined for each reflectance measurement, and a drift correction is determined periodically and then applied to a plurality of reflectance measurements. A different drift correction may, however, be determined for each reflectance measurement if time permits.

The reflectance property indication may be obtained from the original reflectance measurement or from the reflectance measurement as corrected by the corrections. The reflectance property indication may be expressed as an absolute value of reflectance, such as, for example, a value of a diffuse blue reflectance. Alternatively, the reflectance property indication may be expressed as a relative value of reflectance, such as, for example, a diffuse blue reflectance factor or ISO brightness as provided for in ISO standard ISO 2470.

In the preferred embodiment, the apparatus of the invention is adapted for use in making a reflectance measurement of a lignocellulosic pulp on a pulp production finishing line. More particularly, in the preferred embodiment the apparatus of the invention is adapted for use in making a reflectance measurement of a formed pulp product as it moves along a pulp production finishing line between a forming press and a bale press. The apparatus of the invention may also be adapted for use in obtaining a reflectance property indication from the reflectance measurement.

Even more particularly, in the preferred embodiment, the housing is adapted to be installed on the pulp production finishing line such that the formed pulp product passes the viewing port as the formed pulp product moves along the pulp production finishing line between the forming press and the bale press.

In the preferred embodiment, the formed pulp product defines a measurement surface which is comprised of an underside of the formed pulp product. As a result, in the preferred embodiment the housing is adapted to be installed on the pulp production finishing line so that the measurement surface of the formed pulp product is adjacent to the viewing port when the formed pulp product passes the housing on the pulp production finishing line.

As a result, in the preferred embodiment, the housing is installed underneath a transport table of a transport section which connects the forming press and the bale press so that the viewing port faces upward. Preferably the housing is installed underneath a third or subsequent transport table of the transport section of the pulp production finishing line.

The housing is preferably substantially closed so that the interior of the housing is substantially isolated from the exterior of the housing. In the preferred embodiment, the apparatus is further comprised of a movable shutter associated with the viewing port, wherein the shutter is movable between an open position in which the viewing port is open and a closed position in which the viewing port is closed.

Preferably the reflectometer is movable within the interior of the housing so that the measurement direction of the reflectometer may be selectively aligned with the viewing port or with a reference standard which is positioned within the interior of the housing. More preferably the reflectometer is movable within the interior of the housing so that the measurement direction of the reflectometer may be selectively aligned with the viewing port or with one of a plurality of reference standards.

In the preferred embodiment, a high reflectance reference standard and a low reflectance reference standard are positioned within the interior of the housing and the reflectometer is movable within the interior of the housing so that the measurement direction may be selectively aligned with the viewing port, with the high reflectance reference standard, or with the low reflectance reference standard.

The reflectometer may be movable within the interior of the housing in any manner. Preferably the reflectometer is rotatably movable within the interior of the housing. In the preferred embodiment the apparatus is further comprised of a rotatable mount for mounting the reflectometer within the interior of the housing. In the preferred embodiment the apparatus is further comprised of a motor for moving the reflectometer.

The reflectometer defines a measurement aperture and the measurement direction of the reflectometer is defined by the measurement aperture.

In the preferred embodiment, the apparatus is further comprised of an aperture window for sealing the measurement aperture to prevent contaminants from entering the reflectometer. The aperture window has an interior side and an exterior side.

In the preferred embodiment, the apparatus is further comprised of a cleaning mechanism for cleaning the exterior side of the aperture window to remove contaminants which may enter the housing through the viewing port and gather on the aperture window. The cleaning mechanism may be comprised of any structure, apparatus or device which is suitable for cleaning the exterior side of the aperture window.

In the preferred embodiment the cleaning mechanism which cleans the aperture window is also configured to clean the reference standards. Alternatively, if cleaning the reference standards is considered necessary or desirable, a separate cleaning mechanism may be provided to clean the reference standards.

In the preferred embodiment, the cleaning mechanism is comprised of a source of pressurized gas for directing a gas stream over the exterior side of the aperture window to clean the aperture window. In the preferred embodiment the gas is air.

The apparatus is further comprised of a light source for directing light within the reflectometer. The light source may be any source of light which is suitable for use with the reflectometer and with the type of measurements of reflectance which are to be made by the reflectometer. For example, if the reflectance measurement is a direct reflectance measurement, the light source is comprised of a type of source of light which is capable of providing light in a specific desired direction.

In the preferred embodiment, the reflectometer is configured to measure diffuse reflectance in order to provide a diffuse reflectance or a diffuse blue reflectance as the reflectance measurement. In the preferred embodiment, the light source is comprised of a plurality of light emitting diodes which are arranged circumferentially around the measurement aperture. In the preferred embodiment the apparatus is further comprised of a diffuser for diffusing the light provided by the light emitting diodes so that the light source and the diffuser together provide a source of diffuse light.

The apparatus is preferably further comprised of a presence sensing device for sensing the sample. In the preferred embodiment, the presence sensing device is configured to sense a formed pulp product as it moves along the pulp production finishing line.

The presence sensing device may be comprised of any structure, device or apparatus which is capable of sensing the sample. In the preferred embodiment the presence sensing device is comprised of a presence sensor.

The presence sensing device is positioned relative to the housing so that the reflectometer can be prepared for making the reflectance measurement when the sample passes the viewing port of the housing. In the preferred embodiment where the housing is installed underneath the third transport table of the transport section of the pulp production finishing line, the presence sensor is positioned ahead of the housing.

In the preferred embodiment, the apparatus is further comprised of a distance measuring device for obtaining a distance measurement of an actual distance between the sample and the reflectometer. In the preferred embodiment the actual distance between the sample and the reflectometer is defined as the distance between the measuring surface of the formed pulp product and the receptor of the reflectometer.

The distance measuring device may be comprised of any structure, device or apparatus which is capable of providing the distance measurement. The distance measuring device is positioned such that the distance measuring device can view the measurement surface of the formed pulp product and can provide a measurement of distance which can be referenced to the position of the reflectometer.

In the preferred embodiment, the apparatus is further comprised of a memory. The memory may be configured to store the reflectance measurement, corrections to the reflectance measurement, the reflectance property indication, and/or information regarding the pulp production finishing line and the formed pulp products. Preferably the memory stores the reflectance measurement so that the reflectance measurement can be processed to obtain a reflectance property indication from the reflectance measurement.

In the preferred embodiment, the apparatus is her comprised of a processor for correcting the reflectance measurement in order to obtain the reflectance property indication. The processor may be comprised of a single structure, device or apparatus or may be comprised of a plurality of structures, devices or apparatus.

In the preferred embodiment, the apparatus is also further comprised of at least one controller for controlling the apparatus. The apparatus may be controlled so that it is fully automated or the apparatus may be controlled so that it is only partially automated. In the preferred embodiment, the apparatus is substantially fully automated, and requires manual intervention only when servicing of the apparatus is required.

The processor and/or the controller may be comprised of one or more programmable logic controllers, personal computers, microcontrollers, microprocessors etc. In the preferred embodiment, the processor and the controller are comprised of at least one programmable logic controller and at least one personal computer.

In the preferred embodiment, the apparatus is configured to provide that the measurement direction of the reflectometer is aligned with the viewing port upon the sensing of the sample by the presence sensing device.

In the preferred embodiment, the apparatus is configured so that a reflectance measurement of a formed pulp product is made by the reflectometer upon the sensing of the formed pulp product by the presence sensing device.

In the preferred embodiment, the apparatus is further configured so that the viewing port is open when the reflectance measurement is made. The apparatus may also be configured so that the viewing port is closed at times when a reflectance measurement is not being made. Preferably the apparatus is configured so that the viewing port is closed at all times when a reflectance measurement of a sample is not being made by the reflectometer, in order to minimize the amount of contaminants which enter the housing through the viewing port.

The apparatus may be configured so that the reflectance measurement is comprised of a single measurement of observed reflectance of the sample. In the preferred embodiment, the apparatus is configured so that the reflectance measurement is comprised of an average of a plurality of measurement of an observed reflectance of the formed pulp product over the measurement surface. As a result, in the preferred embodiment, the apparatus is configured so that the reflectometer makes a plurality of measurements of the observed reflectance of each formed pulp product.

Similarly, the apparatus may be configured so that the distance measurement is comprised of a single measurement of the actual distance between the sample and the reflectometer. In the preferred embodiment, the apparatus is configured so that the distance measurement is comprised of an average of a plurality of measurement of the actual distance between the measurement surface and the reflectometer over the measurement surface. As a result, in the preferred embodiment, the apparatus is configured so that the distance measuring device makes a plurality of measurements of the actual distance between the measurement surface and the reflectometer for each formed pulp product.

In the preferred embodiment, both the method and apparatus of the invention provide an automated system for obtaining reflectance property indications of formed pulp products on a pulp production finishing line.

DETAILED DESCRIPTION

The present invention is comprised of a method and apparatus for obtaining a reflectance property indication of a sample. The sample is preferably comprised of a lignocellulosic material. In a preferred embodiment the sample is comprised of a lignocellulosic pulp.

In the preferred embodiment the method and apparatus are used in connection with a pulp production finishing line and are used for obtaining a reflectance property indication of a pulp sample on the pulp production finishing line. The method and apparatus are, however, not restricted to use in connection with a pulp production finishing line, and are generally applicable for obtaining a reflectance property indication of any type of sample.

The reflectance property indication may be expressed as a brightness of the pulp. In the preferred embodiment, the reflectance property indication is comprised of a diffuse blue reflectance factor of the pulp, and is preferably substantially equivalent to a diffuse blue reflectance factor or ISO brightness as provided for in ISO standard ISO 2470.

The method and apparatus of the invention provide for making a reflectance measurement of the pulp and then correcting the reflectance measurement to obtain the reflectance property indication. The reflectance measurement represents an observed reflectance of the pulp and the reflectance property indication represents a standardized reflectance of the pulp.

Figure 1:
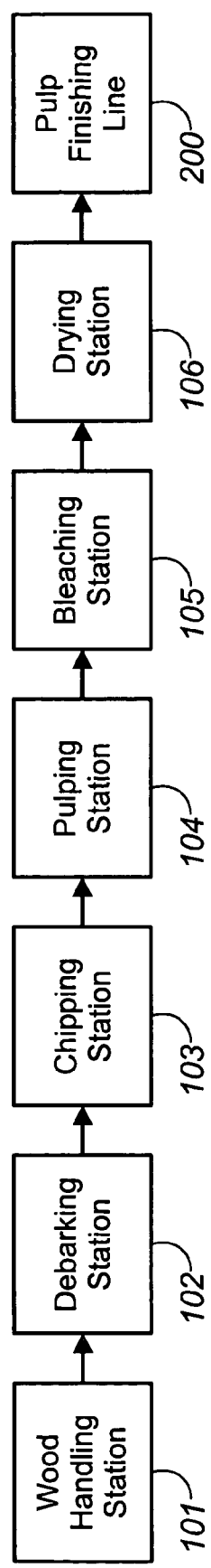
FIG. 1 is a block diagram depicting the basic steps of a typical pulp production process.

Referring to FIG. 1, there is provided a block diagram depicting the basic steps of a typical pulp production process. The process for producing pulp involves transformation of wood or some other lignocellulosic material into a fibrous material, hereafter referred to as "pulp".

A raw material such as logs is first received at a wood handling station (101). The raw material is cut at the wood handling station (101) and is then sent for debarking at a debarking station (102). The debarked raw material is then transferred to a chipping station (103) where the debarked raw material is slashed into wood chips. The wood chips are then transferred to a pulping station (104) for the production of raw pulp.

Different methods of producing pulp have been developed, including both chemical pulping methods and mechanical pulping methods. Some examples of pulp production methods include refiner mechanical pulping (RMP), thermo-mechanical pulping (TMP), thermal refiner mechanical pulping (TRMP), and bleached chemo-thermo-mechanical pulping (BCTMP).

In RMP, pulp is produced by mechanical reduction of wood chips in a disc refiner. When wood chips are submitted to the action of rotating discs of a mechanical refiner, the wood chips are progressively broken down into finer particles and into wood fibers. A variation of RMP is TMP, in which the wood chips are submitted to hot steam before and during the refining process, and in which both heating and refining are performed under increased pressure. When heating and refining are performed under atmospheric pressure, the process is referred to as thermal refiner mechanical pulping (TRMP). The steam applied in the TMP process serves to soften the wood chips and results in raw pulp with a greater percentage of long fibers and less shives, when compared to pulp produced by RMP. When the wood chips are treated with hot steam and a bleaching chemical before refinement, the process is then referred to as bleached chemo-thermo-mechanical pulping (BCTMP).

The pulp in connection with which the invention is used is preferably pulp produced according to the BCTMP process, but the method and apparatus of the invention are also applicable to pulp produced by other types of pulping processes.

The raw pulp produced at the pulping station (104) is transferred to a bleaching station (105), where treatment of the raw pulp with one or more bleaching agents, such as for example hydrogen peroxide, chlorine dioxide, oxygen and caustic soda, is alternated with washing filter cycles.

The bleached pulp is then sent for drying at a drying station (106). Possible methods of drying the bleached pulp include heat drying or pressure drying. Pulp leaving the drying station 106 is referred to as fluff pulp. The fluff pulp is sent to a pulp production finishing line (200), where it is pressed into bales and prepared for shipping.

Figure 2:
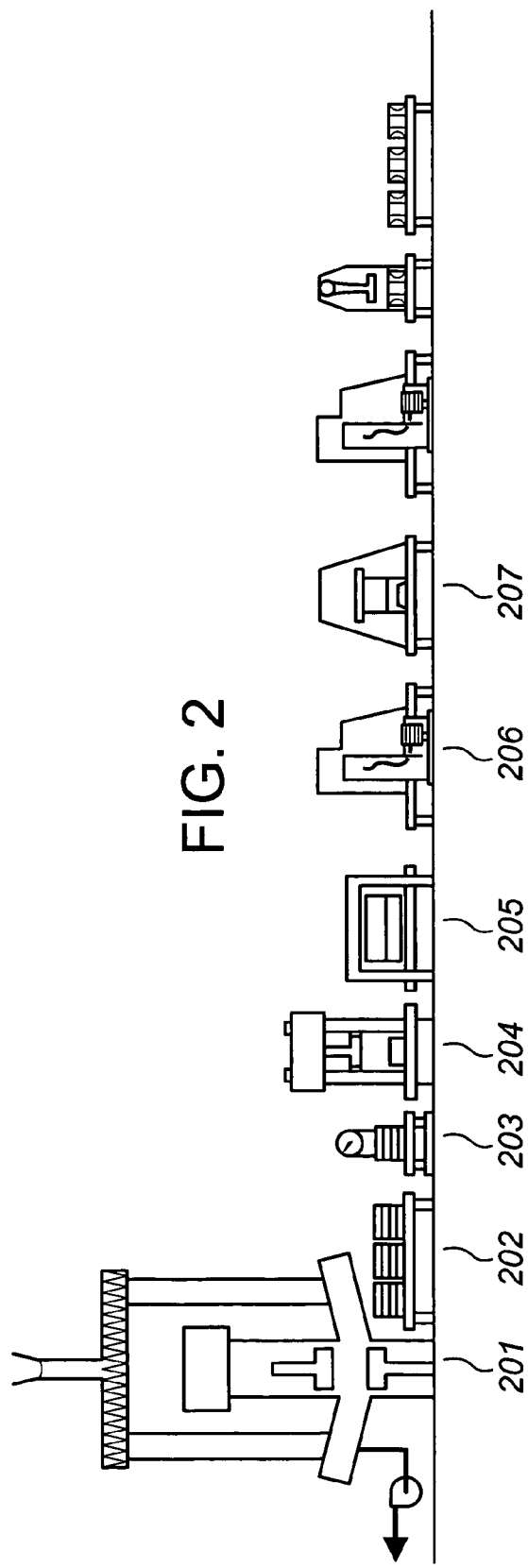
FIG. 2 is a schematic block diagram of a typical pulp production finishing line.

Referring to FIG. 2, there is provided a schematic block diagram depicting a typical pulp production finishing line (200). A first amount of fluff pulp is introduced into a forming press (201), and is pressed into a first thin layer of a pulp cookie. A second amount of fluff pulp is then added on top of the first thin layer of the pulp cookie, and the forming press (201) presses the second amount of fluff pulp into a second thin layer of the pulp cookie.

Typically, the above process is repeated several times to produce a formed pulp product comprising a pulp cookie having several layers. Depending on the physical properties of the fluff pulp, a pulp cookie contains up to four or more layers of fluff pulp. A pulp cookie is produced in layers because the volume of an amount of fluff pulp contained in four or more layers of a pulp cookie is typically too large to be introduced into the forming press (201) as a single amount all at once.

After the pulp cookie is formed, the formed pulp product is transferred to a transport section (202), which typically comprises three or more transport tables linked in series for conveying the formed pulp product. In FIG. 2, a single transport table is shown so that FIG. 2 can depict substantially all of the components of the pulp production finishing line (200).

The formed pulp product is transferred via the transport section (202) to a scale (203). At the scale (203), the formed pulp product is weighed to confirm whether the formed pulp product satisfies specified weight requirements. From the scale (203), the formed pulp product is sent to a bale press (204) where the formed pulp product is pressed to produce a pulp bale.

The bale press (204) is an important component of the pulp production finishing line (200). The purpose of the bale press (204) is to mechanically compress the formed pulp product by applying pressures reaching and even exceeding 5000 pounds per square inch (psi), in order to reduce its volume for shipping. As a result, the top layer of a pulp bale leaving the bale press (204) has been pressed twice, (i.e., once in the forming press (201) and once in the bale press (204)), and other layers of the pulp bale have been pressed at least twice, with the exact number depending on the total number of layers of the formed pulp product which was submitted to the bale press (204).

A pulp bale leaving the bale press (204) is sent sequentially to a wrapping machine (205) for wrapping with plastic, a tying machine (206) for tying the pulp bale with a suitable material, and a marking machine (207). At the marking machine (207), the pulp bale is provided with a bale label which typically includes a lot number and information regarding quality parameters of the pulp bale, such as bulk and pulp strength. The pulp bale as a final pulp product is then ready for shipment.

In a preferred embodiment, the method and the apparatus of the invention are used to obtain a reflectance property indication which is applicable to a pulp on a pulp production finishing line and which is obtained by making reflectance measurements of the pulp on the pulp production finishing line.

Since a formed pulp product is moved along the transport section (202) of a pulp production finishing line, and since the underside of the formed pulp product provides a smooth flat surface which is formed during the formation of the formed pulp product, a reflectance property indication relating to the pulp on the pulp production finishing line may be obtained by making a reflectance measurement of the formed pulp product while the formed pulp product is moving along the transport section (202) between the forming press (201) and the bale press (204).

It has been found that the third or subsequent table of the transport section (202) is often most suitable for making the reflectance measurement since most loose fibers from the formed pulp product tend to fall from the formed pulp product while the formed pulp product is traveling on the first two tables of the transport section (202).

The reflectance (i.e., brightness) of a material such as a pulp sample is inversely related to the surface particle density of the individual fiber particles which constitute the surface of the pulp sample. Consequently, as a pressure applied to the pulp sample increases, the surface particle density increases and the reflectance of the pulp sample decreases. Conversely, when the pressure applied to the pulp sample is released, the surface particle density decreases and the reflectance of the pulp sample increases.

It may therefore be expected that the reflectance of a pulp sample will change with variations in the surface texture of the pulp sample. More specifically, a relatively smooth surface texture (i.e., a relatively high surface particle density) will typically result in a lower reflectance than a relatively rough surface texture (i.e., a relatively low surface particle density).

Figure 3:
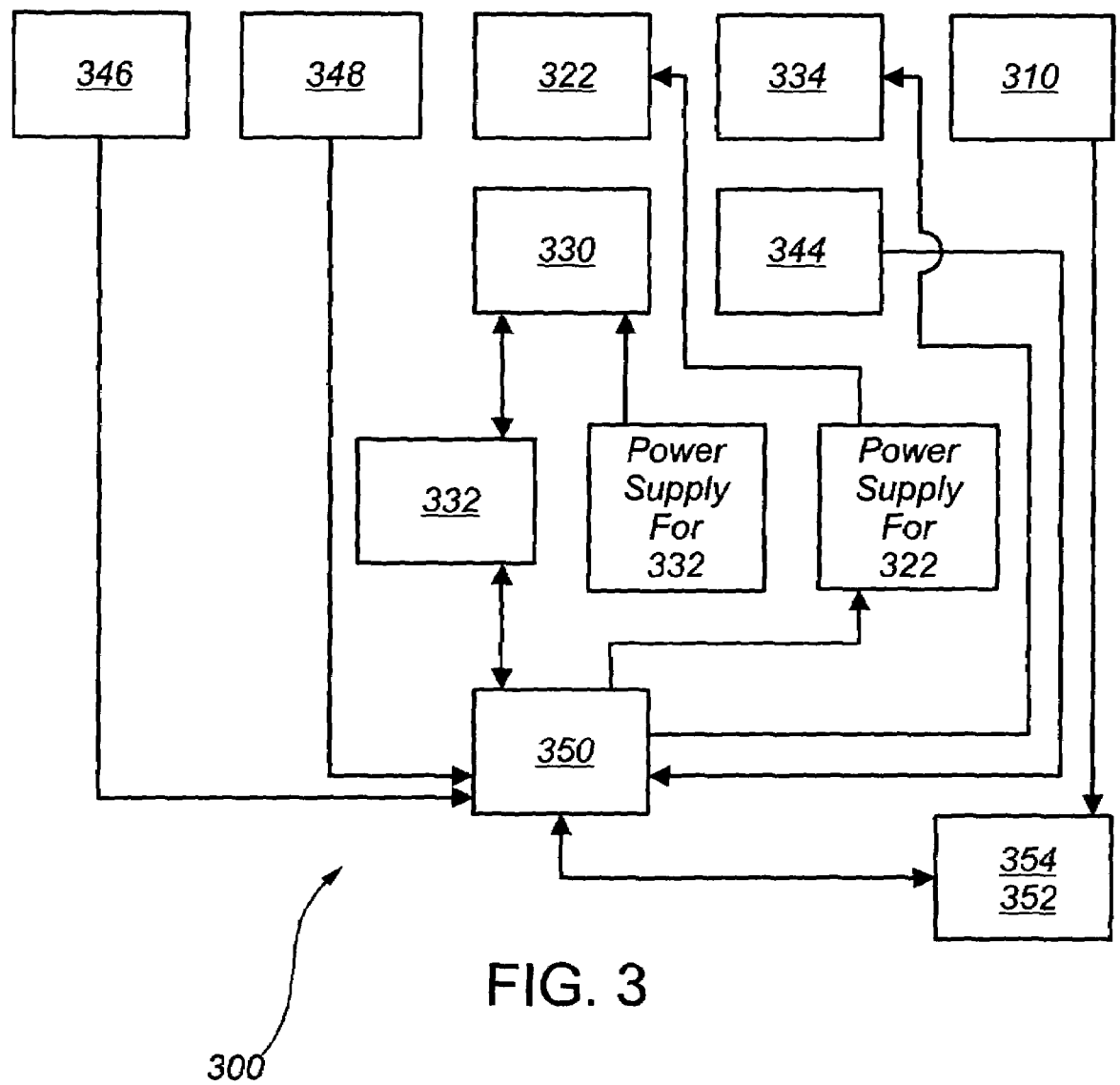
FIG. 3 is a block diagram depicting components of a system according to a preferred embodiment of the apparatus of the invention.
Figure 4:
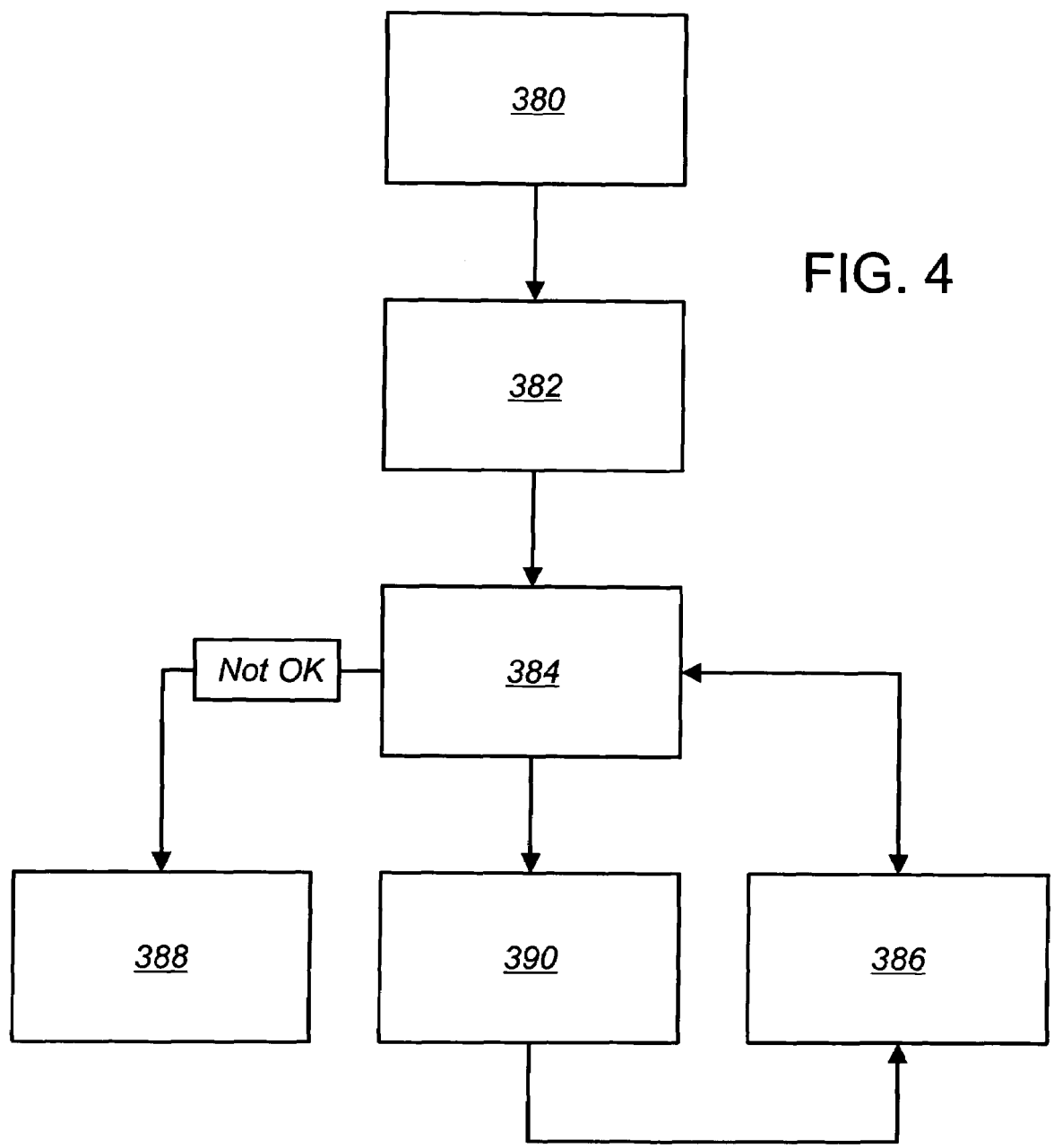
FIG. 4 is a flow chart of procedures for operating a system according to a preferred embodiment of the apparatus of the invention.
Figure 5:
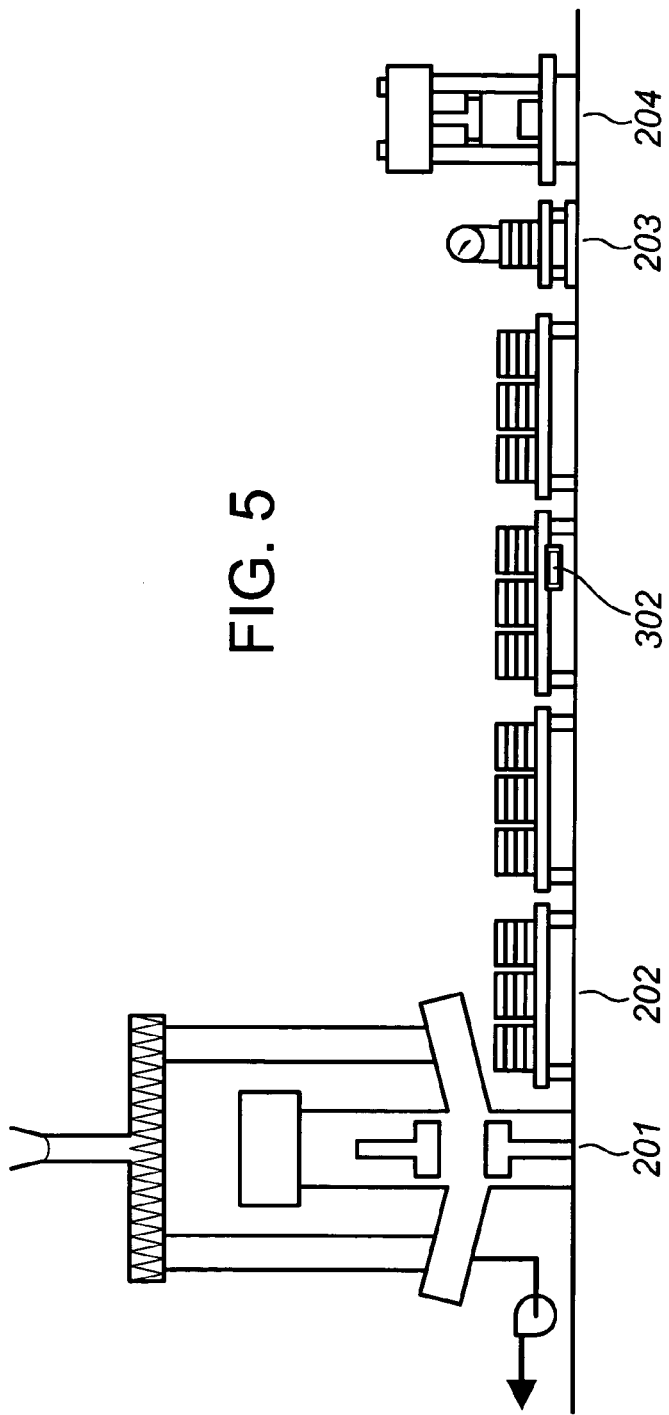
FIG. 5 is a schematic block diagram of a typical pulp production finishing line depicting the preferred location of a housing of a system according to a preferred embodiment of the apparatus of the invention.
Figure 6:
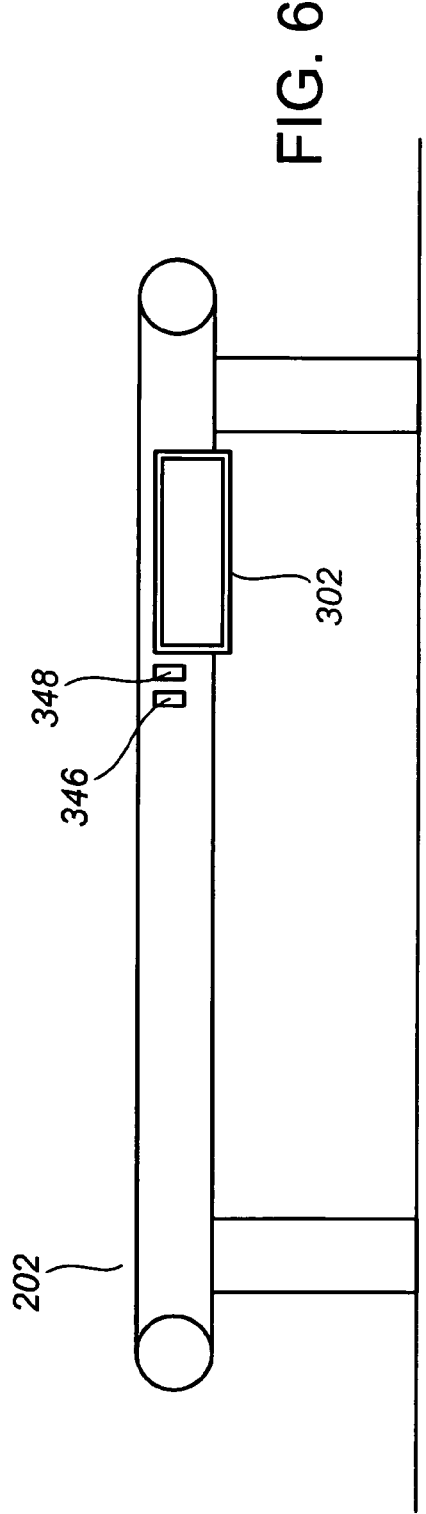
FIG. 6 is a schematic drawing of components of a preferred embodiment of components of a system according to a preferred embodiment of the apparatus of the invention positioned on a pulp production finishing line.
Figure 7:
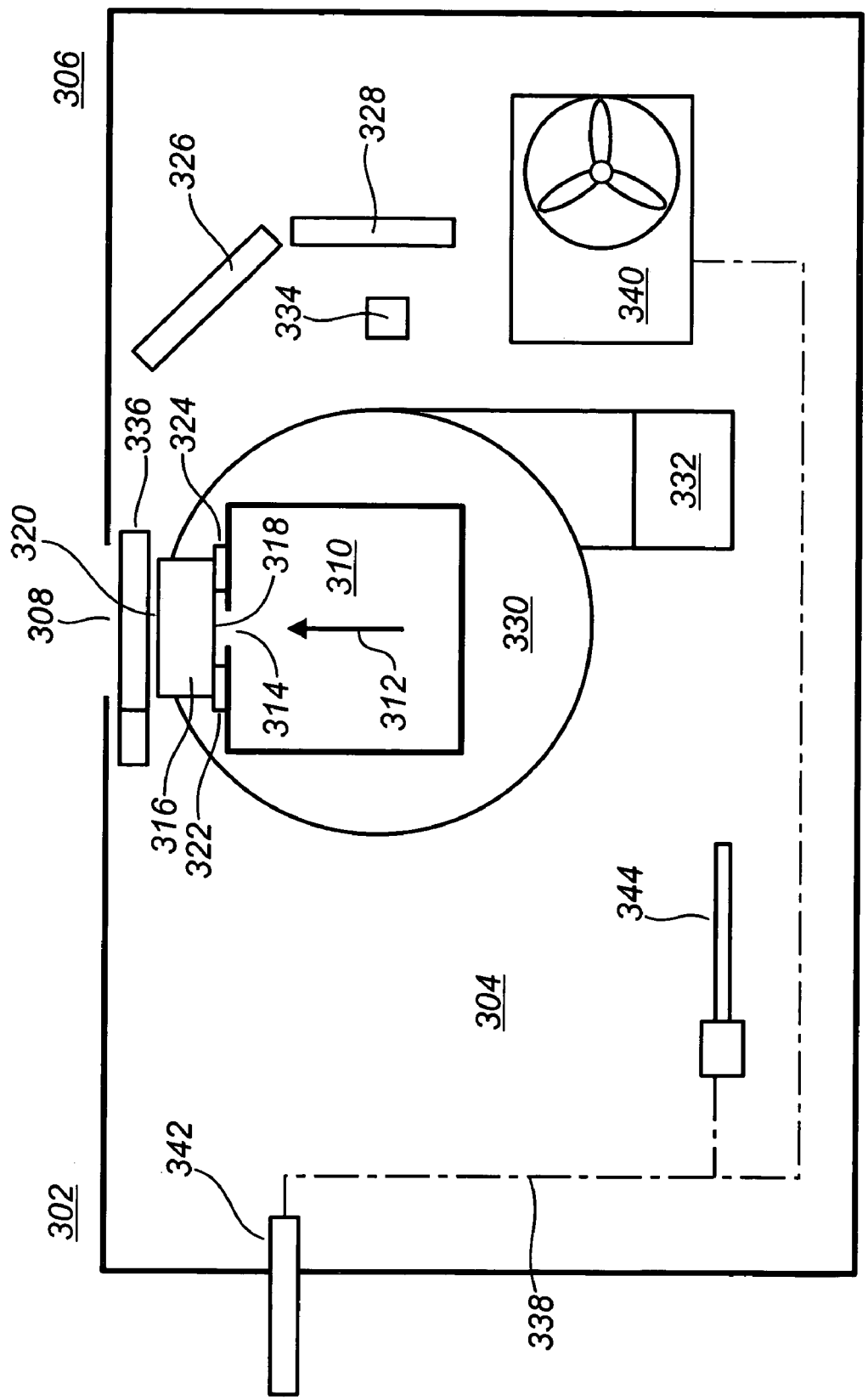
FIG. 7 is a schematic drawing of an interior of a housing according to a preferred embodiment of the apparatus of the invention.

Referring to FIG. 3, there is provided a block diagram depicting components of a system comprising a preferred embodiment of the apparatus of the invention Referring to FIGS. 5-7, there is provided schematic drawings of components comprising a preferred embodiment of the apparatus of the invention. Referring to FIG. 4, there is provide a flow chart of procedures for operating a system comprising an apparatus according to the preferred embodiment of the invention.

In the preferred embodiment as depicted in FIGS. 3-7, the system, apparatus and method are configured to make a reflectance measurement of a formed pulp product as a sample on a pulp production finishing line and to obtain a reflectance property indication for the formed pulp product from the reflectance measurement. In the preferred embodiment, the reflectance measurement is a diffuse reflectance or a diffuse blue reflectance and the reflectance property indication is substantially equivalent to a diffuse blue reflectance factor as provided for in ISO standard ISO 2470.

Referring to FIG. 7, the preferred embodiment of an apparatus (300) of the invention is comprised of a housing (302). Referring to FIG. 5 and FIG. 6, the housing (302) is adapted to be installed on a pulp production finishing line (200) between the forming press (201) and the bale press (204). More specifically, the housing (302) is adapted to be installed underneath the third transport table in the transport section (202) of the pulp production finishing line (200). In the preferred embodiment the housing (302) is installed using a supporting chain and is positioned to provide a space of about twenty (20) millimeters between the viewing port (308) and an underside of a formed pulp product (not shown) which may be moving along the transport table.

The housing (302) defines an interior (304) of the housing (302), an exterior (306) of the housing (302), and a viewing port (308). The housing (302) is oriented so that the viewing port (308) faces upward.

The interior (304) of the housing (302) contains an optical reflectometer (310). In the preferred embodiment the reflectometer (310) is configured to conform substantially with ISO standard ISO 2469, and is thus configured to make reflectance measurements of a diffuse reflectance. In the preferred embodiment the reflectometer (310) has a detection range of between about 200 nanometers and about 800 nanometers.

As provided for in ISO 2469, the reflectometer (310) comprises an integrating sphere. The reflectometer (310) has a measurement direction (312), which is the direction in which reflectance measurements are made by the reflectometer (310). The measurement direction is defined by a measurement aperture (314). The measurement aperture (314) is provided with an aperture window (316) for sealing the measurement aperture (314). The aperture window (316) has an interior side (318) and an exterior side (320).

The apparatus (300) is further comprised of a light source (322) for directing light within the reflectometer (310). In the preferred embodiment, the light source (322) is comprised of a plurality of light emitting diodes arranged circumferentially around the measurement aperture (314). In the preferred embodiment, the apparatus is further comprised of a diffuser (324) for diffusing the light provided by the light source (322). The diffuser (324) is located adjacent to the light emitting diodes and around the measurement aperture (314) so that the light source (322) and the diffuser (324) together provide a source of diffuse light.

A high reflectance reference standard (326) and a low reflectance reference standard (328) are contained within the interior (304) of the housing (302). The high reflectance reference standard (326) may represent a perfect reflecting diffuser as described in ISO standard ISO 2470. The low reflectance reference standard (328) may represent a perfect absorbing diffuser. The high reflectance reference standard (326) and the low reflectance reference standard (328) may therefore provide a range of diffuse blue reflectance factor or ISO brightness of between 100 percent and 0 percent. Alternatively, the high reflectance reference standard (326) and the low reflectance reference standard (328) may provide only relatively higher and lower reflectance.

The reflectometer (310) is mounted within the interior (304) of the housing (302) on a rotatable mount (330). The rotatable mount (330) enables the reflectometer (310) to rotatably move within the interior (304) of the housing (302) so that the measurement direction of the reflectometer (310) may be selectively aligned with the viewing port (308), with the high reflectance reference standard (326), or with the low reflectance reference standard (328). A motor (332) such as a stepper motor is provided within the interior (304) of the housing (302) to drive the rotatable mount (330) and thus move the reflectometer (310).

A cleaning mechanism (334) is provided within the interior (304) of the housing (302) for cleaning the exterior side (320) of the aperture window (316). The cleaning mechanism (334) is comprised of a source of a pressurized gas. In the preferred embodiment the pressurized gas is preferably air. The cleaning mechanism (334) is used to clean from the exterior side (320) of the aperture window (316) contaminants which enter the housing (302) via the viewing port (308).

In the preferred embodiment, the cleaning mechanism (334) is configured also to clean the high reflectance reference standard (328) and the low reflectance reference standard (328) as may be required. Alternatively, a separate cleaning mechanism (not shown) may be provided for cleaning the high reflectance reference standard (326) and the low reflectance reference standard (328).

The housing (302) is substantially closed so that the interior (304) of the housing (302) is substantially isolated from the exterior (306) of the housing (302). To assist in closing the housing (302), the apparatus (300) is provided with a movable shutter (336) which is associated with the viewing port (308). The shutter (336) is movable between an open position in which the viewing port (308) is open and a closed position in which the viewing port (308) is closed. The shutter (336) prevents contaminants from falling into the interior (304) of the housing (302) except when the viewing port (308) is open.

The apparatus (300) is provided with a temperature control mechanism (338) for controlling a temperature within the interior (304) of the housing (302). In preferred embodiments, the temperature control mechanism (338) is comprised of a heater (340), a cooler (342) and a temperature sensor (344). In the preferred embodiment the cooler (342) is comprised of a vortex cooler. The temperature control mechanism (338) enables the temperature within the interior (304) of the housing to be maintained within a range which is suitable for operation of the reflectometer (310).

The apparatus (300) is further comprised of a presence sensing device (346) for sensing a formed pulp product as it moves along the pulp production finishing line (200). In the preferred embodiment the presence sensing device (346) is comprised of a presence sensor which is positioned ahead of the third transport table in the transport section (202) of the pulp production finishing line (200).

The apparatus (300) is further comprised of a distance measuring device (348) for obtaining a distance measurement of an actual distance between the underside of the formed pulp product and the reflectometer (310). In the preferred embodiment the distance measuring device (348) is positioned such that the distance measuring device (348) can view the underside of the formed pulp product as it moves along the pulp production finishing line (200) and such that the distance between the distance measuring device (348) and the reflectometer (310) is known, so that the measurements obtained by the distance measuring device (348) can be referenced to the position of the reflectometer (310), thereby providing measurements of the actual distance between the underside of the formed pulp product and the reflectometer (310).

In the preferred embodiment, the actual distance between the underside of the formed pulp product and the reflectometer (310) is defined as the distance between the underside of the formed pulp product and the receptor (not shown) of the reflectometer (310) as defined by ISO standard ISO 2469. In the preferred embodiment, the distance measuring device (348) is offset from the receptor of the reflectometer (310) by a known distance so that the measurements obtained by the distance measuring device (348) can be converted to a measurement of the actual distance between the formed pulp product and the reflectometer (310).

Referring to FIG. 3, the apparatus (300) is further comprised of a programmable logic controller (PLC) (350) and a personal computer (352) as controllers for controlling the apparatus (300).

The programmable logic controller (350) receives inputs from the temperature sensor (344), the presence sensing device (346), the distance measuring device (348) and the personal computer (352) and generates outputs for controlling the reflectometer (310), the light source (322), the cleaning mechanism (334) and the temperature control mechanism (338) in response thereto. The programmable logic controller (350) also provides communication between the personal computer (352) and the pulp production line control system (not shown).

The personal computer (352) receives data from the reflectometer (310) and from the programmable logic controller (350). The personal computer (352) provides output signals to the programmable logic controller (350) to control the programmable logic controller (350) and also functions as a processor by processing the data received from the reflectometer (310) and from the programmable logic controller (350).

More particularly, the personal computer (352) receives reflectance and distance data pertaining to formed pulp products, processes the data to provide reflectance measurements of the formed pulp products, and corrects the reflectance measurements to obtain reflectance property indications of the formed pulp product. The personal computer (352) includes a memory (354) for storing the received data and/or the processed received data.

The programmable logic controller (350), the personal computer (352) and the necessary power supplies for the apparatus (300) are positioned outside the housing (302), are located remote of the housing (302) and are therefore not shown on FIGS. 5-7.

The apparatus (300) is configured so that the measurement direction (312) of the reflectometer (310) is aligned with the viewing port (308) upon the sensing of a formed pulp product by the presence sensing device (346), thus preparing the apparatus (310) to make a reflectance measurement of the formed pulp product. If the measurement direction (312) is not aligned with the viewing port (308) when the formed pulp product is sensed by the presence sensing device (346), the programmable logic controller (350) sends a control command to the motor (332) to cause the reflectometer (310) to rotate on the rotatable mount (330) to align the measurement direction (312) with the viewing port (308). If the measurement direction (312) is already aligned with the viewing port (308) when the formed pulp product is sensed by the presence sensing device (346), no movement of the reflectometer (310) is necessary.

The apparatus (300) is also configured so that a reflectance measurement of the sample is made by the reflectometer (310) upon the sensing of the formed pulp product by the presence sensing device (346). The apparatus (300) is also configured so that the viewing port (308) is open when the reflectance measurement of the sample is made.

The operation of the apparatus (300) is described with reference to FIG. 4. First, the components of the apparatus (300) are switched on and the apparatus (300) undergoes an initial diagnostic check (380) to confirm that all components are switched on.

Second, the apparatus (300) undergoes a warm-up procedure (382). During the warm-up procedure (382), the cleaning mechanism (334) cleans the exterior side (320) of the aperture window (316) and the reference standards (326, 328), the temperature within the interior (304) of the housing (302) is adjusted to about 23 degrees Celsius, and the reflectometer (310) is moved into alignment with one of the reflectance standards (326 or 328) to confirm that the reflectometer (310) and the light source (322) are functioning.

Third, the apparatus (300) undergoes a system status check (384) in which the sensitivity of the reflectometer (310) and the intensity of the light source (322) are evaluated by moving the reflectometer (310) so that the measurement direction (312) is sequentially in alignment with each of the high reflectance reference standard (326) and the low reflectance reference standard (328) and checking the actual reflectance range of the reflectance standards (326,328) against a calibrated or standard reflectance range.

If the actual reflectance range of the reflectance standards (326,328) is outside of acceptable limits, the apparatus (300) may undergo a routine automatic calibration procedure (386), in which the aperture window (316) is re-cleaned and the actual reflectance range of the reflectance standards (326, 328) is brought within acceptable limits.

If the routine automatic calibration procedure (386) is unsuccessful or if otherwise warranted, the apparatus (300) may undergo a system service procedure (388) in which the apparatus may be serviced and/or calibrated manually.

Following the system status check (384) or if required, the routine automatic calibration procedure (386) and/or the system service procedure (388), the apparatus (300) enters a measurement mode (390) in which the apparatus (300) is ready to make reflectance measurements of formed pulp products and to obtain reflectance property indications from the reflectance measurements.

As a formed pulp product moves along the pulp production finishing line (200) and is sensed by the presence sensing device (346), an input signal is sent to the programmable logic controller (350) and to the personal computer (352) that a new measurement is to begin. The reflectometer (310) is positioned so that the measurement direction (312) is aligned with the viewing port (308) and the shutter (336) is moved to the open position so that the viewing port (308) is open.

The underside of the formed pulp product defines a flat measurement surface (not shown) which results from the forming of the formed pulp product in the forming press (201). As the measurement surface of the formed pulp product moves over the viewing port (308), a series of measurements of the observed reflectance of the formed pulp product are made by the reflectometer (310) and stored in the memory (354). Similarly, a series of measurements of the actual distance between the measurement surface and the reflectometer (310) are made by the distance measuring device (348) and are stored in the memory (354).

The apparatus (300) may be configured to make only a single measurement of the reflectance of the measurement surface of each formed pulp product as the reflectance measurement of the formed pulp product. Preferably, however, a plurality of measurements of the observed reflectance over the measurement surface are made, and an average of the measurements is used as the reflectance measurement of the formed pulp product. In the preferred embodiment, approximately fifteen (15) measurements of the observed reflectance of the measurement surface are made of each formed pulp product, and an average of the fifteen (15) measurements is used as the reflectance measurement of the formed pulp product. In the preferred embodiment, the measurements of reflectance and the measurements of distance are made as the formed pulp product moves along the pulp production finishing line, with the result that each of the measurements is made of a different location on the measurement surface of the formed pulp product.

Similarly, a single measurement of the actual distance between the measurement surface of the formed pulp product and the reflectometer may be used as a distance measurement. Preferably, however, a plurality of measurements of the actual distance over the measurement surface are made and an average of the measurements is used as the distance measurement for the formed pulp product. In the preferred embodiment, approximately eighty (80) measurements of the actual distance between the measurement surface and the reflectometer (310) are made of each formed pulp product, and an average of the eighty (80) measurements is used as the distance measurement for the formed pulp product. As will be seen in the description of the method of the invention, a plurality of measurements of actual distance is also useful in the preferred embodiment for making a texture correction of the reflectance measurement.

After the measurements of observed reflectance and actual distance are made for a formed pulp product, the apparatus (300) waits for the presence sensing device (346) to sense a new formed pulp product moving along the pulp production finishing line (200). While the apparatus (300) is waiting for a new formed pulp product, the apparatus (300) may, if necessary or desirable, undergo the routine automatic calibration process (386). In the preferred embodiment, during continuous use the apparatus (300) undergoes the routine automatic calibration process (386) approximately every fifteen (15) minutes or approximately every thirty (30) formed pulp products.

Once the measurements of observed reflectance of the formed pulp product and the actual distance between the measurement surface of the formed pulp product and the reflectometer (310) have been made, the measurements may be processed using the method of the invention in order to obtain the reflectance property indication for the formed pulp product.

In the preferred embodiment the reflectance property indication is substantially equivalent to a diffuse blue reflectance factor or "ISO brightness" as provided for in ISO standard ISO 2470. As a result, in the preferred embodiment the purpose of processing the measurements is to correct the observed reflectance of the formed pulp product to account for a difference between a standardized reflectance of the formed pulp product in accordance with ISO standard ISO 2470 and the observed reflectance of the formed pulp product as measured by the reflectometer (310).

The preferred embodiment of the method of the invention for obtaining the reflectance property indication of the formed pulp product from the measurements of the observed reflectance of the formed pulp product is now described.

Development of Distance Correction Functions

The correlation between reflectance and distance is determined before the apparatus (300) is operating on the pulp production finishing line (200) in order to develop one or more distance correction functions which represent reflectance as a function of distance. In the preferred embodiment the distance correction functions are developed in a laboratory using an apparatus as described in ISO standard ISO 2469.

In order to develop the distance correction functions, a plurality of handsheets exhibiting a range of ISO brightness are prepared in accordance with TAPPI standard TAPPI 218. The observed reflectance of each of the handsheets over a range of distances between the handsheet and the reflectometer are determined in accordance with ISO standard 2469 and ISO standard 2470. Each handsheet thus yields a separate distance correction function.

For each handsheet, the observed reflectance as defined by the weighting function in Equation (1) is recorded for each handsheet over the range of distances between the handsheet and the reflectometer:

$$\mathrm{Re} f_{ISO} = \frac{\sum (\mathrm{Re} f_\lambda * F(\lambda))}{\sum F(\lambda)} \qquad (1)$$

where:
F(λ) is the relative spectral distribution function of the reflectometer as defined in ISO standard 2470
Re $f_\lambda$ is the reflectance of the handsheet at a specified wavelength of light
Re $f_{ISO}$ is the diffuse blue reflectance of the handsheet at the particular distance The distance correction functions yielded by the handsheets may be expressed as linear functions or as non-linear functions (such as second order polynomial functions). In the preferred embodiment the distance correction functions are expressed as linear functions. The distance correction functions may be described graphically or algebraically.

Figure 8:
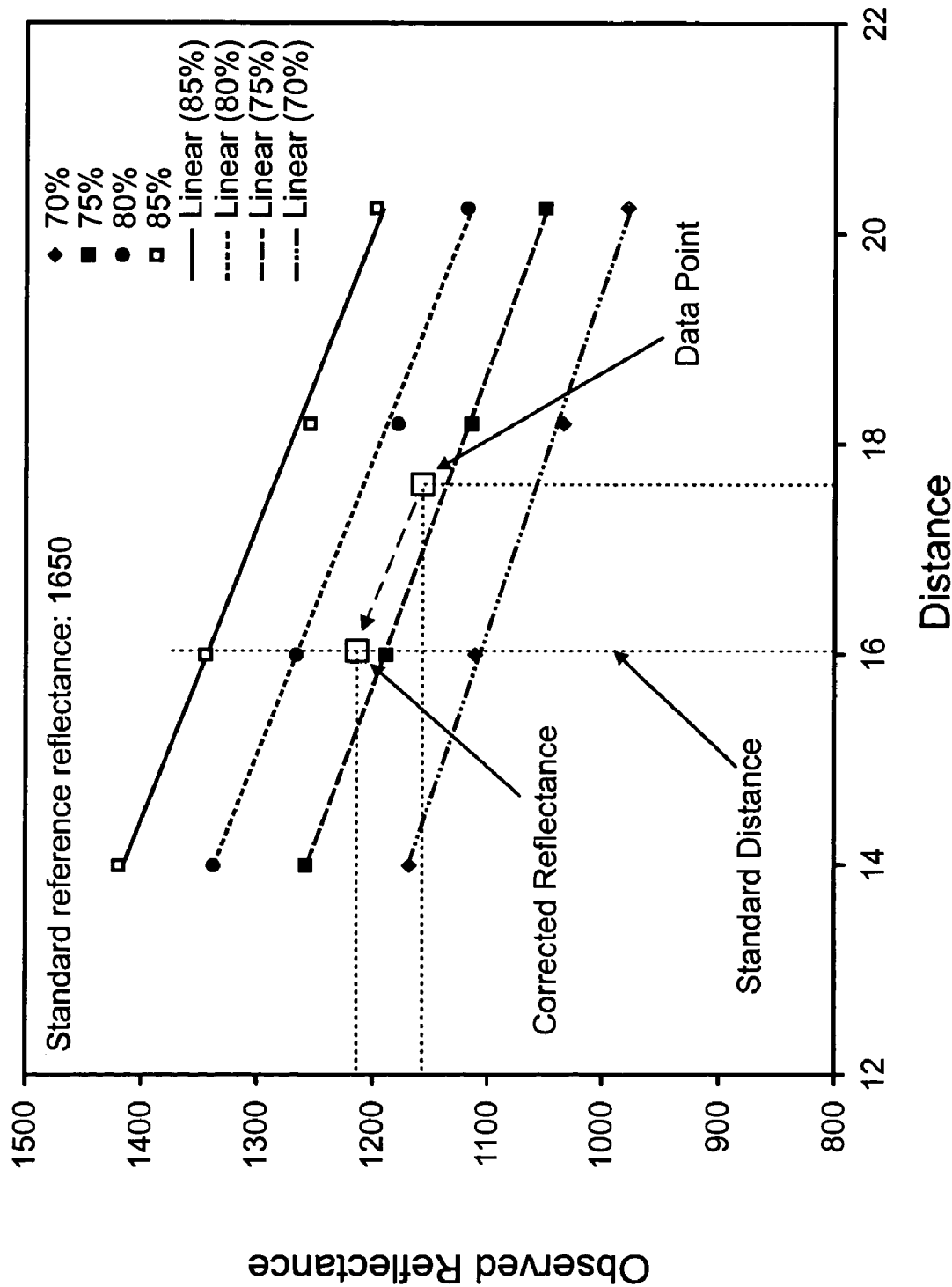
FIG. 8 is a graph providing a graphical representation of a distance correction according to a preferred embodiment of the method of the invention.

Referring to FIG. 8, a graph depicting exemplary graphical representations of distance correction functions is provided. FIG. 8 is for illustrative purposes only and does not represent actual data.

In FIG. 8, four linear curves are depicted. Each curve represents a different handsheet and thus a separate distance correction function. In each curve, observed reflectance of the handsheet is expressed as a function of the actual distance between the handsheet and the reflectometer.

Each handsheet and thus each carve relates to a pulp having a different known ISO brightness. Each curve therefore represents variations in observed reflectance as a function of actual distance for a pulp having a particular known ISO brightness. As a result, at the standard distance required by ISO standard ISO 2469 and/or ISO standard ISO 2470, which is depicted in FIG. 8 as 16 millimeters, the observed reflectance of each curve will coincide with the standardized reflectance of the handsheet.

Determination of the Reflectance Measurement of the Formed Pulp Product

The reflectance measurement (Re $f_{avg}$) is the average of the measurements of the observed reflectance of the measurement surface of the formed pulp product, calculated as follows:

$$\mathrm{Re} f_{avg} = \frac{\sum \mathrm{Re} f_{(l)}}{n} \qquad (2)$$

where:
Re $f_{(l)}$ is a measurement of the observed reflectance of the formed pulp product
n is the number of measurements made of the observed reflectance In the preferred embodiment, Re $f_{avg}$ represents diffuse blue reflectance. As a result, if the measurements of the reflectance of the measurement surface are measurements of total reflectance, the measurements may be processed in a similar manner as set out in Equation (1) above in order to obtain measurements of diffuse blue reflectance.

Determination of the Distance Measurement of the Formed Pulp Product

The distance measurement is the average of the measurements of the actual distance between the measurement surface of the formed pulp product and the reflectometer (310), calculated as follows:

$$d(\mathrm{actual})_{avg} = \frac{\sum d(\mathrm{actual})_i}{n} \qquad (3)$$

where:
d(actual)$_i$ is a measurement of the actual distance between the measurement surface of the formed pulp product and the reflectometer (310)
n is the number of measurements made of the actual distance Distance Correction of the Reflectance Measurement Once the distance correction functions have been developed, they may be used to make distance corrections for formed pulp products on the pulp production finishing line. In order to make a distance correction for a particular formed pulp product, the following procedure is used.

First, a distance data point consisting of the distance measurement (d(actual)$_{avg}$) between the measurement surface and the reflectometer (310) and the reflectance measurement (Re $f_{avg}$) of the formed pulp product is established.

Second, a distance correction function which fits with the distance data point is then selected. The distance correction function which is selected may be a function based upon an actual handsheet (i.e., one of the four functions depicted in FIG. 8), or may be a distance correction function which represents an interpolation or an extrapolation of the distance correction functions developed from the handsheets.

Third, the distance correction is made by identifying from the selected distance correction function the observed reflectance which corresponds to the standard distance. This observed reflectance is the distance corrected reflectance measurement of the formed pulp product.

Development of Drift Correction Functions

In the preferred embodiment, the apparatus (300) is configured to operate within an operating range of light intensity. Within this operating range, reflectance measurements (Re $f_{avg}$) obtained by the apparatus (300) may be corrected for "drift" in light intensity of the light source (322).

In the preferred embodiment, the operating range of the apparatus (300) is defined by the observed reflectance of the high reflectance reference standard (326). For example, in the preferred embodiment the operating range of the apparatus (300) may be defined as a reflectance within a range of between about 1600 and about 1650 as exhibited by the high reflectance reference standard (326).

The correlation between reflectance and light intensity is also determined before the apparatus (300) is operating on the pulp production finishing line (200) in order to develop one or more drift correction functions which represent reflectance as a function of light intensity. In the preferred embodiment the drift correction functions are developed using the apparatus (300) and using the same or similar handsheets as those used to develop the distance correction functions.

In order to develop the drift correction functions, a plurality of handsheets exhibiting a range of ISO brightness are prepared in accordance with TAPPI standard TAPPI 218. The observed reflectance of each of the handsheets over a range of light intensities are determined using the apparatus (300) of the invention. The range of light intensities is within the operating range of the apparatus (300) and is expressed as the observed reflectance of the high reflectance reference standard (326).

As in the case of the distance correction, each handsheet yields a separate drift correction function.

As in the case of the distance correction, for each handsheet, the observed reflectance as defined by the weighting function in Equation (4) is recorded for each handsheet over the range of distances between the handsheet and the reflectometer.

$$\mathrm{Re} f_{ISO} = \frac{\sum (\mathrm{Re} f_\lambda * F(\lambda))}{\sum F(\lambda)} \quad (4)$$

where:
   $F(\lambda)$ is the relative spectral distribution function of the reflectometer as defined in ISO standard 2470
   $\mathrm{Re}\, f_\lambda$ is the reflectance of the handsheet at a specified wavelength of light
   $\mathrm{Re}\, f_{ISO}$ is the diffuse blue reflectance of the handsheet at the particular distance The drift correction functions yielded by the handsheets may be expressed as linear functions or as non-linear functions (such as second order polynomial functions). In the preferred embodiment the distance correction functions are expressed as linear functions. The distance correction functions may be described graphically or algebraically.

Figure 9:
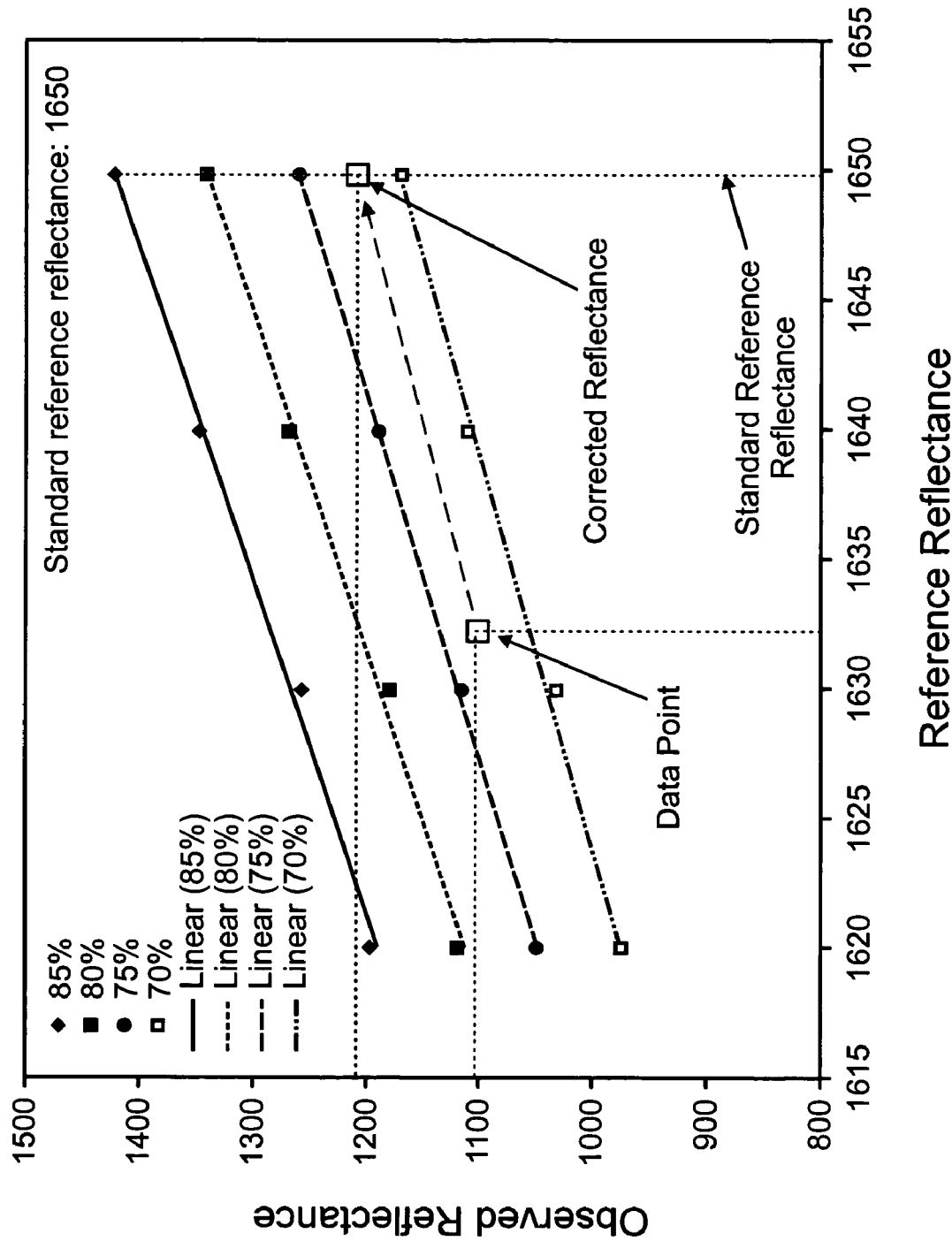
FIG. 9 is a graph providing a graphical representation of a drift correction according to a preferred embodiment of the method of the invention.

Referring to FIG. 9, a graph depicting exemplary graphical representations of drift correction functions is provided. FIG. 9 is for illustrative purposes only and does not represent actual data.

In FIG. 9, four linear curves are depicted. Each curve represents a different handsheet and thus a separate drift correction function. In each curve, observed reflectance of the handsheet is expressed as a function of the reflectance of the high reflectance reference standard (326).

Each handsheet and thus each curve relates to a pulp having a different known ISO brightness. Each curve therefore represents variations in observed reflectance as a function of the reflectance of the high reflectance reference standard (326). As a result, at the standard reflectance of the high reflectance reference standard (326), which is depicted in FIG. 9 as 1650, the observed reflectance of each curve will coincide with the standardized reflectance of the handsheet.

Drift Correction of the Reflectance Measurement

Once the drift correction functions have been developed, they may be used to make drift corrections for formed pulp products on the pulp production finishing line. In order to make a drift correction for a particular formed pulp product, the following procedure is used.

First, a drift data point consisting of the reflectance of the high reflectance reference standard (326) and the reflectance measurement ($\mathrm{Re}\, f_{avg}$ or the distance corrected $\mathrm{Re}\, f_{avg}$) of the formed pulp product is established.

Second, a drift correction function which fits with the drift data point is then selected. The drift correction function which is selected may be a function based upon an actual handsheet (i.e., one of the four functions depicted in FIG. 9), or may be a drift correction function which represents an interpolation or an extrapolation of the drift correction functions developed from the handsheets.

Third, the drift correction is made by identifying from the selected drift correction function the observed reflectance which corresponds to the standard reflectance of the high reflectance reference standard (326). This observed reflectance is the drift corrected reflectance measurement of the formed pulp product.

Calculation of the Standard Deviation of the Measurements of Actual Distance

The standard deviation of the measurements of the distance between the measurement surface of the formed pulp product and the reflectometer (310) is calculated as a distance standard deviation value $d_{SD}$.

$$d_{SD} = \sqrt{\frac{\sum (d_i - d_{avg})^2}{(\sum i) - 1}} \quad (5)$$

The distance standard deviation value ($d_{SD}$) provides information relating to the surface texture of the measurement surface of the formed pulp product and is therefore used to perform a texture correction of the reflectance measurement.

Development of Texture Correction Functions

The reflectance of a formed pulp product and the reflectance of a handsheet of an equivalent pulp prepared in accordance with TAPPI standard TAPPI 218 may be different due to the respective textures of the formed pulp product and the handsheet. Generally, a formed pulp product will have a higher texture (i.e., will be less smooth) than a handsheet of an equivalent pulp prepared in accordance with TAPPI standard TAPPI 218. Generally, a pulp having a higher texture will exhibit a higher reflectance than an equivalent pulp having a lower texture.

It has been found that distance standard deviation ($d_{SD}$) provides an acceptable measure of the texture of both a formed pulp product and a handsheet which can be used to make a texture correction of the reflectance measurement ($\mathrm{Re}\, f_{avg}$, the distance corrected $\mathrm{Re}\, f_{avg}$, or the distance and drift corrected $\mathrm{Re}\, f_{avg}$).

The texture of the measurement surface of a formed pulp product is dependent upon the characteristics of both the structure and the operation of the forming press (201) and upon the characteristics of the pulp of which the formed pulp product is comprised.

For example, each forming press (201) will provide a unique texture "fingerprint" on the measurement surface of the formed pulp product, due to the material used in the bottom platen of the forming press (201) and any irregularities in the surface of the bottom platen of the forming press (201).

In addition, the texture of the measurement surface of the formed pulp product will vary according to the grade or type of pulp contained in the formed pulp product. For example, brighter pulps tend to be less stiff than less bright pulps, with the result that brighter and thus less stiff pulps tend to conform more to the bottom platen of the forming press (201) than do less bright and more stiff pulps.

In the preferred embodiment the texture correction is dependent upon the development of one or more texture correction functions which relate to the specific forming press (201) which is used on the pulp production finishing line (200) and to the types or grades of pulp which are produced in the particular mill. The texture correction functions are developed through experience from the specific pulp production finishing line and from testing of samples of pulp prepared in accordance with TAPPI standard TAPPI 218.

In order to develop the texture correction functions, a plurality of sets of formed pulp products from the pulp production finishing line exhibiting a range of ISO brightness (as determined using ISO standard ISO 2469 and ISO standard ISO 2470) are evaluated using the apparatus (300). The observed reflectance of a set of formed pulp products having an equivalent ISO brightness but exhibiting different values of distance standard deviation ($d_{SD}$) is used to develop each texture correction function. Different sets of formed pulp products exhibiting different ISO brightness are therefore used to provide different texture correction functions.

The texture correction functions yielded by the sets of formed pulp products may be expressed as linear functions or as non-linear functions (such as second order or higher order polynomial functions). In the preferred embodiment the texture correction functions are expressed as second order polynomial functions. The texture correction functions may be described graphically or algebraically.

Figure 10:
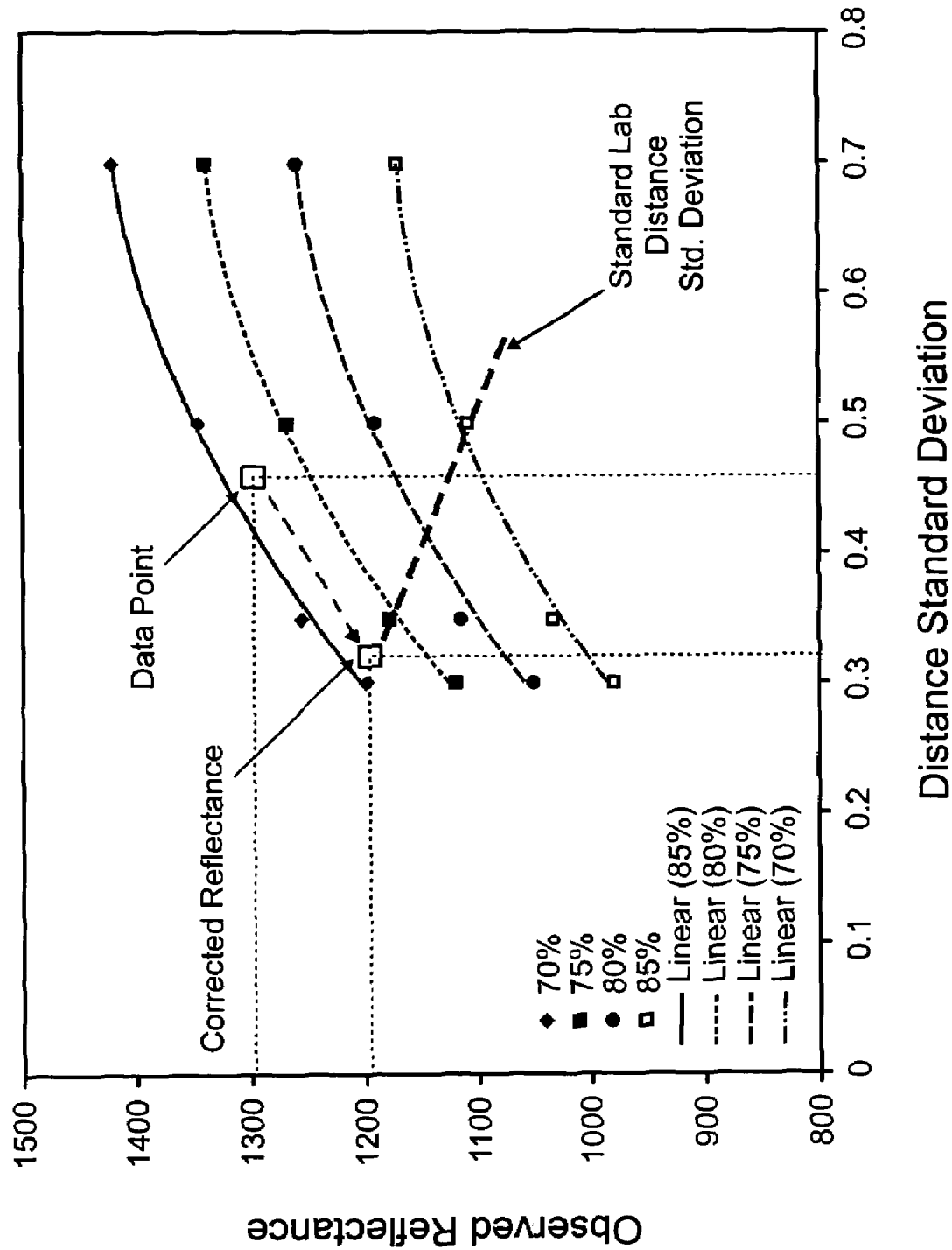
FIG. 10 is a graph providing a graphical representation of a texture correction according to a preferred embodiment of the method of the invention.

Referring to FIG. 10, a graph depicting exemplary graphical representations of texture correction functions is provided. FIG. 10 is for illustrative purposes only and does not represent actual data.

In FIG. 10, four second order curves are depicted. Each curve represents a different set of formed pulp products having a common ISO brightness, and thus a separate texture correction function. In each curve, observed reflectance of the formed pulp products is expressed as a function of the distance standard deviation ($d_{SD}$) of the formed pulp products.

Each set of formed pulp products and thus each curve represents variations in observed reflectance as a function of the distance standard deviation ($d_{SD}$) of formed pulp products having a particular known ISO brightness. As a result, at the distance standard deviation ($d_{SD}$) of a sample prepared in accordance with TAPPI standard TAPPI 218 (which is depicted by a dashed line in FIG. 10), the observed reflectance of each curve will coincide with the standardized reflectance of the pulp.

Texture Correction of the Reflectance Measurement

Once the texture correction functions have been developed, they may be used to make texture corrections for formed pulp products on the pulp production finishing line. In order to make a texture correction for a particular formed pulp product, the following procedure is used.

First, a texture data point consisting of the distance standard deviation ($d_{SD}$) of the formed pulp product and the reflectance measurement (Re $f_{avg}$, the distance corrected Re $f_{avg}$, Re $f_{avg}$) of the formed pulp product is established.

Second, a texture correction function which fits with the texture data point is then selected. The texture correction function which is selected may be a function based upon an actual set of formed pulp products (i.e., one of the four functions depicted in FIG. 10), or may be a texture correction function which represents an interpolation or an extrapolation of the texture correction functions developed from the sets of formed pulp products.

Third, the texture correction is made by identifying from the selected texture correction function the observed reflectance which corresponds to the distance standard deviation ($d_{SD}$) of a sample prepared in accordance with TAPPI standard TAPPI 218. This observed reflectance is the texture corrected reflectance measurement of the formed pulp product.

Obtaining the Reflectance Property Indication

The reflectance property indication of a formed pulp product may be obtained by correcting the reflectance measurement (Re $f_{avg}$) of the formed pulp product by making the distance correction, the drift correction and the texture correction as set out above, thus providing a distance, drift and texture corrected reflectance measurement (Re $f_{avg}$).

Figure 11:
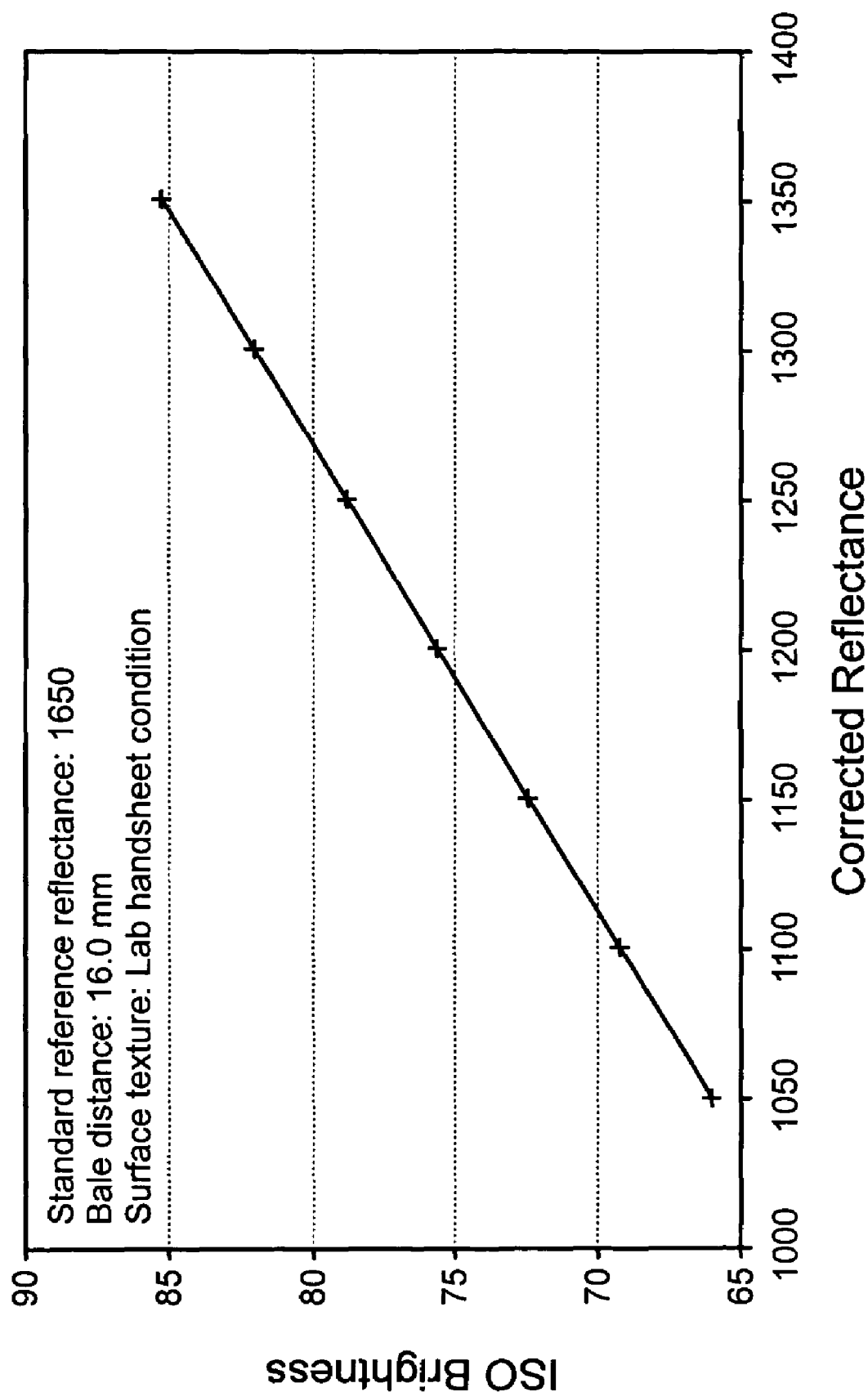
FIG. 11 is a graph providing a graphical representation of obtaining a reflectance property indication from a corrected reflectance measurement according to a preferred embodiment of the method of the invention.

Referring to FIG. 11, a graph depicting a graphical representation of obtaining a reflectance property indication from a corrected reflectance measurement (Re $f_{avg}$) is provided. FIG. 11 is for illustrative purposes only and does not represent actual data.

Referring to FIG. 11, in the preferred embodiment the reflectance property indication of the formed pulp product is obtained by referencing the distance, drift and texture corrected reflectance measurement (Re $f_{avg}$) to the reflectance of a perfect reflecting diffuser as defined in ISO standard ISO 2470, so that the reflectance property indication is substantially equivalent to a diffuse blue reflectance factor or ISO brightness as determined in accordance with ISO standard ISO 2469 and ISO standard ISO 2470.

In this document, the word "comprising" is used in its non-limiting sense to mean that items following the word are included, but items not specifically mentioned are not excluded. A reference to an element by the indefinite article "a" does not exclude the possibility that more than one of the elements is present, unless the context clearly requires that there be one and only one of the elements.

The embodiments of the invention in which an exclusive property or privilege is claimed are defined as follows:

1. A method for obtaining a reflectance property indication of a sample, wherein the sample is comprised of a lignocellulosic material, the method comprising:
    (a) providing an optical reflectometer;
    (b) relatively positioning the sample and the reflectometer;
    (c) making a reflectance measurement of the sample with the reflectometer, wherein the reflectance measurement represents an observed reflectance of the sample; and
    (d) correcting the reflectance measurement in order to obtain the reflectance property indication, wherein the reflectance property indication represents a standardized reflectance of the sample, wherein correcting the reflectance measurement accounts for a difference between the standardized reflectance of the sample and the observed reflectance of the sample, and wherein correcting the reflectance measurement is comprised of making a correction selected from the group of corrections consisting of a geometry correction, a texture correction, a drift correction, and combinations thereof.

2. The method as claimed in claim 1 wherein the lignocellulosic material is comprised of a lignocellulosic pulp.

3. The method as claimed in claim 2 wherein the reflectance measurement is a measurement of a diffuse reflectance.

4. The method as claimed in claim 3 wherein the reflectance property indication is comprised of a diffuse blue reflectance factor.

5. The method as claimed in claim 4 wherein correcting the reflectance measurement is comprised of making a geometry correction to correct for a difference between a standard geometry between the sample and the reflectometer and an actual geometry between the sample and the reflectometer.

6. The method as claimed in claim 5 wherein the standard geometry is comprised of a standard distance between the sample and the reflectometer, wherein the actual geometry is comprised of an actual distance between the sample and the reflectometer, and wherein the geometry correction is comprised of a distance correction.

7. The method as claimed in claim 6 wherein the sample defines a measurement surface and wherein making the reflectance measurement is comprised of making a plurality of measurements of the observed reflectance of the sample over the measurement surface and determining an average of the measurements of the observed reflectance as the reflectance measurement.

8. The method as claimed in claim 7 wherein the actual distance between the sample and the reflectometer is comprised of an average actual distance between the measurement surface and the reflectometer.

9. The method as claimed in claim 7 wherein the sample defines a measurement surface and wherein obtaining the distance measurement is comprised of obtaining a plurality of measurements of the actual distance between the measurement surface and the reflectometer and determining an average actual distance between the measurement surface and the reflectometer as the distance measurement.

10. The method as claimed in claim 8 wherein making the distance correction is comprised of:
  (a) obtaining a distance measurement of the actual distance between the sample and the reflectometer;
  (b) establishing a distance data point consisting of the actual distance and the reflectance measurement;
  (c) selecting a distance correction function which fits with the distance data point; and
  (d) making the distance correction from the selected distance correction function.

11. The method as claimed in claim 6 wherein correcting the reflectance measurement is further comprised of making a texture correction to correct for a difference between a standard texture of the sample and an actual texture of the sample.

12. The method as claimed in claim 11 wherein correcting the reflectance measurement is further comprised of making a drift correction to the reflectance measurement to account for a drift in an intensity of a light source which is used to make the reflectance measurement.

13. The method as claimed in claim 6 wherein correcting the reflectance measurement is further comprised of making a drift correction to the reflectance measurement to account for a drift in an intensity of a light source which is used to make the reflectance measurement.

14. The method as claimed in claim 4 wherein correcting the reflectance measurement is comprised of making a texture correction to correct for a difference between a standard texture of the sample and an actual texture of the sample.

15. The method as claimed in claim 14 wherein the sample defines a measurement surface and wherein making the reflectance measurement is comprised of making a plurality of measurements of the observed reflectance of the sample over the measurement surface and determining an average of the measurements of the observed reflectance as the reflectance measurement.

16. The method as claimed in claim 14 wherein making the texture correction is comprised of:
  (a) obtaining a measurement of the actual texture of the sample;
  (b) establishing a texture data point consisting of the actual texture and the reflectance measurement;
  (c) selecting a texture correction function which fits with the texture data point; and
  (d) making the texture correction from the selected texture correction function.

17. The method as claimed in claim 14 wherein the sample defines a measurement surface and wherein obtaining a measurement of the actual texture of the sample is comprised of obtaining a measurement of a distance standard deviation of an actual distance between the measurement surface and the reflectometer.

18. The method as claimed in claim 14 wherein correcting the reflectance measurement is further comprised of making a drift correction to the reflectance measurement to account for a drift in an intensity of a light source which is used to make the reflectance measurement.

19. The method as claimed in claim 4 wherein correcting the reflectance measurement is comprised of making a drift correction to the reflectance measurement to account for a drift in an intensity of a light source which is used to make the reflectance measurement.

20. The method as claimed in claim 19 wherein the sample defines a measurement surface and wherein making the reflectance measurement is comprised of making a plurality of measurements of the observed reflectance of the sample over the measurement surface and determining an average of the measurements of the observed reflectance as the reflectance measurement.

21. The method as claimed in claim 19 wherein the making the drift correction is comprised of referencing the reflectance measurement to a standard reflectance of a reference standard.

22. The method as claimed in claim 21 wherein making the drift correction is comprised of:
  (a) obtaining a reference reflectance measurement of a reference standard;
  (b) establishing a drift data point consisting of the reflectance reference measurement and the reflectance measurement;
  (c) selecting a drift correction function which fits with the drift data point; and
  (d) making the drift correction from the selected drift correction function.

23. The method as claimed in claim 4 wherein the sample is comprised of a lignocellulosic pulp on a pulp production finishing line.

24. The method as claimed in claim 23 wherein the pulp production finishing line is comprised of a forming press for producing a formed pulp product and a bale press for producing a pulp bale from the formed pulp product and wherein the sample is comprised of the formed pulp product.

25. The method as claimed in claim 24 wherein the reflectance measurement is made of an underside of the formed pulp product as the formed pulp product moves along the pulp production finishing line.

26. The method as claimed in claim 3 wherein the reflectance property indication is substantially equivalent to a diffuse blue reflectance factor as provided for in International Standard ISO 2470.

* * * * *

UNITED STATES PATENT AND TRADEMARK OFFICE
CERTIFICATE OF CORRECTION

PATENT NO.        : 7,663,757 B2                                             Page 1 of 1
APPLICATION NO.   : 11/527993
DATED             : February 16, 2010
INVENTOR(S)       : Wei Li et al.

It is certified that error appears in the above-identified patent and that said Letters Patent is hereby corrected as shown below:

Column 11:
Line 38, change "her" to --further--.

Column 17:
Line 5, change "328" to --326--.

Column 27:
Line 10, change "claim 8" to --claim 6--.

Signed and Sealed this

First Day of June, 2010

David J. Kappos
*Director of the United States Patent and Trademark Office*

UNITED STATES PATENT AND TRADEMARK OFFICE
CERTIFICATE OF CORRECTION

PATENT NO. : 7,663,757 B2  Page 1 of 1
APPLICATION NO. : 11/527993
DATED : February 16, 2010
INVENTOR(S) : Li et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 421 days.

Signed and Sealed this

Thirtieth Day of November, 2010

David J. Kappos
*Director of the United States Patent and Trademark Office*